(12) United States Patent
Hodge

(10) Patent No.: US 6,759,221 B1
(45) Date of Patent: Jul. 6, 2004

(54) 14189, A NOVEL HUMAN KINASE AND USES THEREOF

(75) Inventor: Martin R. Hodge, Arlington, MA (US)

(73) Assignee: Millennium Pharmaceuticals, Inc.

( * ) Notice: Subject to any disclaimer, the term of this patent is extended or adjusted under 35 U.S.C. 154(b) by 247 days.

(21) Appl. No.: 09/641,690

(22) Filed: Aug. 18, 2000

(51) Int. Cl.$^7$ .......................... C12N 9/12; C12N 15/54; C07H 21/04
(52) U.S. Cl. .......................... 435/194; 435/183; 435/6; 435/320.1; 435/252.3; 435/325; 435/410; 536/23.1; 536/23.2; 536/23.5
(58) Field of Search ................................ 435/183, 194, 435/320.16, 252.3, 325, 410; 536/23.1, 23.2, 23.5

(56) References Cited

U.S. PATENT DOCUMENTS

| | | | |
|---|---|---|---|
| 6,413,756 B2 * | 7/2002 | Yan et al. | 435/194 |
| 6,416,990 B2 * | 7/2002 | Wei et al. | 435/194 |
| 2001/0051360 A1 | 12/2001 | Wei et al. | |

FOREIGN PATENT DOCUMENTS

| | | |
|---|---|---|
| WO | WO 00/73469 A2 | 12/2000 |
| WO | WO 01/38503 A2 | 5/2001 |
| WO | WO 01/66762 A1 | 9/2001 |
| WO | WO 02/18557 A2 | 3/2002 |

OTHER PUBLICATIONS

NCI–CGAP, Genbank/ EMBL Database, Accession No. BE464560, Jul. 2000.*
Hillier et al., Genbank/EMBL Database, Accession No. AI049667, Jul. 1998.*
Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Abe, Mark K. et al. "ERK8, A New Member of the Mitogen–Activated Protein Kinase Family*" *The Journal of Biological Chemistry*, vol. 277, No. 19, May 10, 2002, pp. 16733–16743.
Strausberg, Robert, "hs84e05.x1", Jul. 27, 2000 (sequence) GenBank [online]. Bethesda, MD, USA: National Center for Biotechnology Information [retrieved on Oct. 3, 2002]. Retrieved from the Internet: <URL: http://www.ncbi.nlm.nih.gov/>. GenBank Accession No. BE464560.

NCBI Accession No. AA284718, Hillier et al., "Generation and Analysis of 280,000 Human Expressed Sequence Tags," *Genome Res.* 1996, pp. 807–828, vol. 6, No. 9.
NCBI Accession No. AF078798, Abe et al., Direct Submission, Submitted Jul. 16, 1998.
NCBI Accession No. AI049667, Hillier et al., 1997, Unpublished.
NCBI Accession No. AI476756, NCI–CGAP, 1999, Unpublished.
NCBI Accession No. AI680380, NCI–CGAP, 1999, Unpublished.
NCBI Accession No. AI921266, NCI–CGAP, 1999, Unpublished.
NCBI Accession No. AR016531, Boulton et al., "Family of MAP2 Protein Kinases,", Jul. 7, 1998, U.S. patent 5,776, 751.
NCBI Accession No. AR036244, Boulton et al., "Family of MAP2 Protein Kinases," Feb. 16, 1999, U.S. patent 5,872, 006.
NCBI Accession No. I34199, Boulton et al., "Family of MAP2 Protein Kinases," Jan. 21, 1997, U.S. patent 5,595, 904.
NCBI Accession No. Q20260, Boulton et al., WO9119008–A, Dec. 12, 1991.
NCBI Accession No. T78543, Young et al., WO9702347–A1, Jan. 23, 1997.
NCBI Accession No. T90352, Young et al., U.S. patent 5,663,313–A, Sep. 2, 1997.
NCBI Accession No. V33561, Young et al., U.S. patent 5,817,479–A, Oct. 6, 1998.
NCBI Accession No. V71030, Kaster et al., WO98/45704–A2, Oct. 15, 1998.

* cited by examiner

*Primary Examiner*—Richard Hutson

(57) ABSTRACT

A novel human kinase protein and nucleic acid molecule is disclosed. In addition to the isolated kinase protein, the invention further provides isolated kinase fusion proteins, antigenic peptides, and anti-kinase antibodies. The invention also provides kinase nucleic acid molecules, recombinant expression vectors containing a nucleic acid molecule of the invention, host cells into which the expression vectors have been introduced, and nonhuman transgenic animals in which a kinase gene has been introduced or disrupted. Diagnostic, screening, and therapeutic methods utilizing compositions of the invention are also provided.

22 Claims, 10 Drawing Sheets

```
                                                              M   C   T   V   V   D   P   R     8
GTTCCGACCMCGCGTCCGCGGACGCGTGGGCGGGCGTCCTGGCCGCC ATG TGC ACC GTA GTG GAC CCT CGC    71

I   V   R   R   Y   L   L   R   R   Q   L   G   Q   G   A   Y   G   I   V   W    28
ATT GTC CGG AGA TAC CTA CTC AGG CGG CAG CTC GGG CAG GGG GCC TAT GGC ATT GTG TGG   131

K   A   V   D   R   R   T   G   E   V   V   A   I   K   K   I   F   D   A   F    48
AAG GCA GTG GAC CGG AGG ACT GGT GAG GTC GTG GCC ATC AAG AAA ATC TTT GAT GCT TTT   191

R   D   K   T   D   A   Q   R   T   F   R   E   I   T   L   L   Q   E   F   G    68
AGG GAT AAG ACA GAT GCC CAG AGA ACA TTC CGG GAA ATC ACG CTC CTC CAG GAG TTT GGG   251

D   H   P   N   I   I   S   L   L   D   V   I   R   A   E   N   D   R   D   I    88
GAC CAT CCC AAC ATC ATC AGC CTC CTT GAC GTG ATC CGG GCA GAG AAC GAC AGG GAC ATT   311

Y   L   V   F   E   F   M   D   T   D   L   N   A   V   I   R   K   G   G   L   108
TAC CTG GTG TTT GAG TTT ATG GAC ACT GAC CTG AAC GCA GTC ATC CGG AAG GGC GGC CTG   371

L   Q   D   V   H   V   R   S   I   F   Y   Q   L   L   R   A   T   R   F   L   128
CTG CAG GAC GTC CAC GTG CGC TCC ATC TTC TAC CAG CTC CTG CGG GCC ACC CGG TTC CTC   431

H   S   G   H   V   V   H   R   D   Q   K   P   S   N   V   L   L   D   A   N   148
CAC TCG GGG CAC GTT GTG CAC CGG GAC CAG AAG CCG TCC AAT GTG CTC CTG GAT GCC AAC   491

C   T   V   K   L   C   D   F   G   L   A   R   S   L   G   D   L   P   E   G   168
TGC ACA GTG AAG CTG TGT GAC TTT GGC CTG GCC CGC TCC CTG GGC GAC CTC CCT GAG GGG   551

P   E   D   Q   A   V   T   E   Y   V   A   T   R   W   Y   R   A   P   E   V   188
CCT GAG GAC CAG GCC GTG ACA GAG TAC GTG GCC ACA CGC TGG TAC CGA GCA CCG GAG GTG   611

L   L   S   S   H   R   Y   T   L   G   V   D   M   W   S   L   G   C   I   L   208
CTG CTC TCT TCG CAC CGA TAC ACC CTT GGG GTG GAC ATG TGG AGT CTG GGC TGT ATC CTG   671

G   E   M   L   R   G   R   P   L   F   P   G   T   S   T   L   H   Q   L   E   228
GGG GAG ATG CTG CGG GGG AGA CCC CTG TTC CCC GGC ACG TCC ACC CTN CAC CAG CTG GAG   731

L   I   L   E   T   I   P   P   P   S   E   E   D   L   L   A   L   G   S   G   248
CTG ATC CTG GAG ACC ATC CCA CCG CCA TCT GAG GAG GAC CTC CTG GCT CTC GGC TCA GGC   791

C   R   A   S   V   L   H   Q   L   G   S   R   P   R   Q   T   L   D   A   L   268
TGC CGT GCC TCT GTG CTG CAC CAG CTG GGG TCC CGG CCA CGA CAG ACG CTG GAT GCC CTC   851

L   P   P   D   T   S   P   E   A   L   D   L   L   R   R   L   V   F   A   288
CTA CCG CCA GAC ACC TCC CCA GAG GCC TTG GAC CTC CTT AGG CGA CTC CTG GTG TTC GCC   911

P   D   K   R   L   S   A   T   Q   A   L   Q   H   P   Y   V   Q   R   F   H   308
CCG GAC AAG CGG TTA AGC GCG ACC CAG GCA CTG CAG CAC CCC TAC GTG CAG AGG TTC CAC   971

C   P   S   D   E   W   A   R   E   A   D   V   R   P   R   A   H   E   G   V   328
TGC CCC AGC GAC GAG TGG GCA CGA GAG GCA GAT GTG CGG CCC CGG GCA CAC GAA GGG GTC  1031

Q   L   S   V   P   E   Y   R   S   R   V   Y   Q   M   I   L   E   C   G   G   348
CAG CTC TCT GTG CCT GAG TAC CGC AGC CGC GTC TAT CAG ATG ATC CTG GAG TGT GGA GGC  1091

S   S   G   T   S   R   E   K   G   P   E   G   V   S   P   S   Q   A   H   L   368
AGC AGC GGC ACC TCG AGA GAG AAG GGC CCG GAG GGT GTC TCC CCA AGC CAG GCA CAC CTG  1151

H   K   P   R   A   D   P   Q   L   P   S   R   T   P   V   Q   G   P   R   P   388
CAC AAA CCC AGA GCC GAC CCT CAG CTG CCT TCT AGG ACA CCT GTG CAG GGT CCC AGA CCC  1211

R   P   Q   S   S   P   G   H   D   P   A   E   H   E   S   P   R   A   A   K   408
AGG CCC CAG AGC AGC CCA GGC CAT GAC CCT GCC GAG CAC GAG TCC CCC CGT GCA GCC AAG  1271

N   V   P   R   Q   N   S   A   P   L   L   Q   T   A   L   G   N   G   E   428
AAC GTT CCC AGG CAG AAC TCC GCT CCC CTG CTC CAA ACT GCT CTC CTA GGG AAT GGG GAA  1331
```

FIGURE 1A

```
      R   P   P   G   A   K   E   A   P   P   L   T   L   S   L   V   K   P   S   G    448
    AGG CCC CCT GGG GCG AAG GAA GCG CCC CCC TTG ACA CTC TCG CTG GTG AAG CCA AGC GGG   1391

R   G   A   A   P   S   L   T   S   Q   A   A   A   Q   V   A   N   Q   A   L    468
    AGG GGA GCT GCG CCC TCC CTG ACC TCC CAG GCT GCG GCT CAG GTG GCC AAC CAG GCC CTG   1451

I   R   G   D   W   N   R   G   G   V   R   V   A   S   V   Q   Q   V   P         488
    ATC CGG GGT GAC TGG AAC CGG GGC GGT GGG GTG AGG GTG GCC AGC GTA CAA CAG GTC CCT   1511

P   R   L   P   P   E   A   R   P   G   R   R   M   F   S   T   S   A   L   Q    508
    CCC CGG CTT CCT CCG GAG GCC CGG CCC GGC CGG AGG ATG TTC AGC ACC TCT GCC TTG CAG   1571

G   A   Q   G   G   A   R   A   L   L   G   Y   S   Q   A   Y   G   T   V         528
    GGT GCC CAG GGG GGT GCC AGG GCT TTG CTT GGA GGC TAC TCC CAA GCC TAC GGG ACT GTC   1631

C   H   S   A   L   G   H   L   P   L   L   E   G   H   V   *                     545
    TGC CAC TCG GCA CTG GGC CAC CTG CCC CTG CTG GAG GGG CAC CAT GTG TGA                1682

GCCGCCCTACTCCCTTCACCTGGCCCTCTGTTCCTGCCCCAGCCCCTTCCCCAGACCCCTCTCCAGTCTCCTGCACCCC   1761

TTAGCCCTCCCTGCTTTGCCTGGCCCGTTGAAGTTCCAGGGAGCTTGCCCGGGTCTCCTCGGGGGAGCAGATGAGGGCC   1840

CTGCCCCCGCCCCACTGACTTTCTCCAATAAAGNCATGTCTGCCCCCCCCCCNAAAAAAAAAAAAAAAAAAAAAA      1914
```

```
GAP of: FrGcgManager_453_GID0yhnfT    check: 7821   from: 1  to: 1998

AF078798 in GenBank to: FrGcgManager_453_HID058iyl    check: 2142   from: 1  to: 1635

Fbh14189a ORF - Import - complete

Symbol comparison table: /ddm_local/gcg/gcg_9.1/gcgcore/data/rundata/nwsgapdna.cmp
CompCheck: 8760

Gap Weight:      12      Average Match:    10.000
     Length Weight:       4      Average Mismatch:  0.000

Quality:   12076            Length:    2022
             Ratio:    7.386             Gaps:      13
Percent Similarity:   77.219   Percent Identity:  77.157

Match display thresholds for the alignment(s):
                     | = IDENTITY
                     : = 5
                     . = 1

FrGcgManager_453_GID0yhnfT x FrGcgManager_453_HID058iyl  June 20, 19100 14:05  ..
```

```
151 ACCATGTGTGCTGCCGAGGTGGACCGTCATGTATCCCAGAGATACCTGAT 200
        |||||  |||  ||||||| ||    ||  ||||||||||   |
  1 .....ATGTGC.ACCGTAGTGGACCCTCGCATTGTCCGGAGATACCTACT 44

201 CAAGCGGAGGCTTGGGAAGGGGGCCTACGGCATTGTATGGAAGGCCATGG 250
     || ||||   |||  |||  |||||||||||  ||||||||  |||||||||   |||
 45 CAGGCGGCAGCTCGGGCAGGGGGCCTATGGCATTGTGTGGAAGGCAGTGG 94

251 ACCGGAGGACTGGTGAGGTAGTGGCCATCAAGAAAATCTTTGATGCCTTT 300
    |||||||||||||||||||||| ||||||||||||||||||||||||||  |||
 95 ACCGGAGGACTGGTGAGGTCGTGGCCATCAAGAAAATCTTTGATGCTTTT 144

301 AGGGACCAGACAGATGCTCAGAGGACCTTCCGTGAAATCATGCTTCTCCG 350
    |||||  ||||||||||| |||||  ||  |||||  |||||||   ||||
145 AGGGATAAGACAGATGCCCAGAGAACATTCCGGGAAATCACGCTCCTCCA 194

351 GGAGTTTGGGGGCCATCCCAACATCATCCGCCTGCTTGATGTAATCCCAG 400
    ||||||||||| |||||||||||||||| ||||| ||||| ||  |
195 GGAGTTTGGGGACCATCCCAACATCATCAGCCTCCTTGACGTGATCCGGG 244

401 CAAAGAATGACAGGGATATTTACCTGGTGTTTGAGTCCATGGACACCGAC 450
```

Figure 2B

```
              ||  ||||  |||||||||  ||||||||||||||||||  ||||||||  |||
245 CAGAGAACGACAGGGACATTTACCTGGTGTTTGAGTTTATGGACACTGAC 294

451 CTGAACGCGGTCATCCAGAAGGGCAGACTGTTGGAGGACATCCACAAACG 500
    ||||||||  |||||||  |||||||  |  |||  ||  |||||  |||||     ||
295 CTGAACGCAGTCATCCGGAAGGGCGGCCTGCTGCAGGACGTCCACGTGCG 344

501 TTGCATCTTTTACCAGCTCCTGAGAGCCACCAAGTTTATCCATTCAGGGC 550
    |  ||||||  |||||||||||||  |  ||||||||  |||  ||||  ||  ||||
345 CTCCATCTTCTACCAGCTCCTGCGGGCCACCCGGTTCCTCCACTCGGGGC 394

551 GCGTCATTCACCGGGACCAGAAGCCAGCCAACGTTCTATTGGATGCTGCT 600
    |||    |  ||||||||||||||||||||  ||||  ||  ||  |||||||
395 ACGTTGTGCACCGGGACCAGAAGCCGTCCAATGTGCTCCTGGATGCCAAC 444

601 TGCCGGGTGAAACTATGTGACTTTGGCCTGGCACGCTCCCTCAGTGACTT 650
    |||   ||||||  ||  |||||||||||||||||||||  ||||||||    |  |||  |
445 TGCACAGTGAAGCTGTGTGACTTTGGCCTGGCCCGCTCCCTGGGCGACCT 494

651 CCCTGA.AGGCCT..GGGCCAGGCCCTGACAGAATATGTGGCCACACGCT 697
    ||||||    |||||    ||  |||||||    |||||||    ||||||||||||||
495 CCCTGAGGGGCCTGAGGACCAGGCCGTGACAGAGTACGTGGCCACACGCT 544

698 GGTACCGAGCTCCAGAGGTGCTTCTGTCTTCCCGATGGTATACCCCTGGG 747
    |||||||||  ||  ||||||||||  ||  ||||||  |    |  ||  ||||  ||||
545 GGTACCGAGCACCGGAGGTGCTGCTCTCTTCGCACCGATACACCCTTGGG 594

748 GTGGACATGTGGAGCCTGGGCTGCATACTGGGAGAGATGCTTCGAGGGCA 797
    |||||||||||||  ||||||||  ||  |||||  ||||||||  ||  |||
595 GTGGACATGTGGAGTCTGGGCTGTATCCTGGGGGAGATGCTGCGGGGGAG 644

798 GCCACTGTTTCCGGGTACATCTACTTTCCACCAGCTGGAGCTGATCCTGG 847
    ||  ||||||  ||  ||  ||  ||  ||  |:|||||||||||||||||||||||
645 ACCCCTGTTCCCCGGCACGTCCACCCTNCACCAGCTGGAGCTGATCCTGG 694

848 AGACCATTCCATTGCCCTCCATGGAGGAGCTCCAGGGCCTTGGATCAGAC 897
    |||||||  |||   |||  ||    ||||||  ||||  ||  ||  ||  |||||  |
695 AGACCATCCCACCGCCATCTGAGGAGGACCTCCTGGCTCTCGGCTCAGGC 744

898 TACAGTGCTTTGATTCTGCAGAATCTTGGATCCAGGCCACGGCAGACGCT 947
    |  |  |||||  |    |  |||||  |  ||  ||  |||  |||||||  ||||||||
745 TGCCGTGCCTCTGTGCTGCACCAGCTGGGGTCCGGCCACGACAGACGCT 794

948 GGACGCCCTCCTGCCGCCAGACACCCCCCCAGAAGCCCTGGACCTCCTCA 997
    |||  ||||||||||  |||||||||||||  |||||||  |||  ||||||||||  |
795 GGATGCCCTCCTACCGCCAGACACCTCCCCAGAGGCCTTGGACCTCCTTA 844

998 AGCGACTCTTGGCATTTGCTCCGGACAAACGGCTTAGTGCAGAGCAGGCT 1047
    ||||||||  |||  ||  ||  |||||||||  |||  |  ||  ||         |||||
845 GGCGACTCCTGGTGTTCGCCCCGGACAAGCGGTTAAGCGCGACCCAGGCA 894
```

Figure 2C

```
1048 CTTCAACACCCTTACGTGCAGAGATTCCATTGCCCCGACCGCGAGTGGAC 1097
     || || ||||| ||||||||||| ||||| ||||||   ||||||| |
 895 CTGCAGCACCCCTACGTGCAGAGGTTCCACTGCCCCAGCGACGAGTGGGC 944

1098 ACGGGGGTCCGATGTGCGGCTCCCGGTACACGAAGGAGACCAGCTCTCTG 1147
     ||| | | | |||||||||| || || |||||||||| ||||||||||||
 945 ACGAGAGGCAGATGTGCGGCCCCGGGCACACGAAGGGGTCCAGCTCTCTG 994

1148 CACCAGAGTATCGCAACCGCCTGTACCAGATGATCCTGGAGCGGAGACGG 1197
     || |||||| |||| |||| | || |||||||||||||||||| | || |
 995 TGCCTGAGTACCGCAGCCGCGTCTATCAGATGATCCTGGAGTGTGGAGGC 1044

1198 AACAGCCGCAGCCCTCGAGAGGAAGACTTGGGGGTTGTGGCCTCGCGGGC 1247
     | |||| ||| | | ||||| | | | || || ||| ||| | |
1045 AGCAGCGGCACCTCGAGAGAGAAGGGCCCGGAGGGTGT...CTCCC...C 1088

1248 AGAGCTCAGGGCTTCCCAGAGGCAATCGCTCAAGCCCGGAGTCCTCCCCC 1297
     | ||| ||||      ||    ||    || ||| ||| |||  | ||| |
1089 A.AGC.CAGG......CA....CACCTGCACAAACCCAGAGCCGACCCTC 1126

1298 AGGTCTTGGCGGAGACGCCTGCGCGGAAACGCGGACCCAAACCTCAGAAT 1347
     || |    |   ||| |||| || |   | | |||||| || ||||
1127 AGCTGCCTTCTAGGACACCTGTGCAGGGTCCCAGACCCAGGCCCCAGAGC 1176

1348 GGCCATGGTCACGA...TCCCGAGCATGTG.................GAA 1377
     ||| || || ||   | ||||||| | |                   |||
1177 AGCCCAGGCCATGACCCTGCCGAGCACGAGTCCCCCCGTGCAGCCAAGAA 1226

1378 .GTTCGCAGGCAGAGTTCAGACCCCCTGTACCAACTTCCGCCGCCAGGCA 1426
     |||| |||||||| || | |||||| |||| | | | ||| |
1227 CGTTCCCAGGCAGAACTCCGCTCCCCTGCTCCAAACTGCTCTCCTAGGGA 1276

1427 GCGGGGAAAGGCCCCCAGGGGCCACAGGGGAGCCACCCTCCGCACCCTCA 1476
     |||||||||||| |||||  |  |  | ||| |||   ||| |||
1277 ATGGGGAAAGGCCCCCTGGGGCGAAGGAAGCGCCCCCCTTGACACTCTCG 1326

1477 GGGGTGAAGACTCACGTTAGGGCGGTGGCGCCCTCCCTGACTTCACAGGC 1526
     ||||||| |  || ||||  | |||||||||||||| || |||||
1327 CTGGTGAAGCCAAGCGGGAGGGGAGCTGCGCCCTCCCTGACCTCCCAGGC 1376

1527 CGCGGCTCAGGCGGCCAATCAGCCTCTGATCCGCAGTGATCCGGCCCGGG 1576
     ||||||||||| ||||||| ||| ||||||||| ||||  |  |||||
1377 TGCGGCTCAGGTGGCCAACCAGGCCCTGATCCGGGGTGACTGGAACCGGG 1426

1577 GCGGTGGGCCAAGGGCTGTCGGCGCGCGACGGGTCCCTTCCCGCCTGCCC 1626
     ||||||||   ||||    | | ||| | || |||||| |||| || ||
1427 GCGGTGGGGTGAGGGTGGCCAGCGTACAACAGGTCCCTCCCCGGCTTCCT 1476

1627 CGGGAGGCCCCGGAACCCCGACCCGGCCGAAGGATGTTTGGCATCTCGGT 1676
```

Figure 2D

```
        I IIIII           IIII IIIIIIII IIIIIIII  III III I
1477 CCGGAGG.........CCCGGCCCGGCCGGAGGATGTTCAGCACCTCTGC 1517

1677 CTCGCAGGGGGCCCAGGGTGCAGCCAGAGCTGCTCTTGGCGGCTACTCCC 1726
     II IIIIII IIIIIIII I  IIIII III   IIIII IIIIIIIII
1518 CTTGCAGGGTGCCCAGGGGGGTGCCAGGGCTTTGCTTGGAGGCTACTCCC 1567

1727 AGGCCTACGGGACCGTGTGCCGCTCCGCGCTGGGCCGCCTGCCTCTGCTC 1776
     I IIIIIIIIII II IIII III II IIIIIII IIIIII IIIII
1568 AAGCCTACGGGACTGTCTGCCACTCGGCACTGGGCCACCTGCCCCTGCTG 1617

1777 CCCGGACCGCGTGCGTGAGCCGCCCACCAACCTCCTTGCGGCAAACTGGC 1826
         II I  I II IIII
1618 GAGGGGCACCATGTGTGA............................... 1635
```

Figure 3A

```
GAP of: FrGcgManager_454_LIDsNLRN_  check: 9383  from: 1 to: 546

4220888 in GenPept to: FrGcgManager_454_MIDOhcGgX  check: 6114  from: 1 to: 545

Fbh14189 aa - Import - complete

Symbol comparison table: /prod/ddm/seqanal/BLAST/matrix/aa/BLOSUM62
CompCheck: 1102
 Matrix made by matblas from blosum62.iij Gap Weight:      12       Average Match:    2.778
       Length Weight:       4       Average Mismatch: -2.248

Quality:    1623              Length:     555
               Ratio:   2.978                Gaps:       5
  Percent Similarity: 69.216     Percent Identity:  66.604

Match display thresholds for the alignment(s):
                    | = IDENTITY
                    : =  2
                    . =  1

FrGcgManager_454_LIDsNLRN_ x FrGcgManager_454_MIDOhcGgX June 20, 19100 14:28   ..

1 MCAAEVDRHVSQRYLIKRRLGKGAYGIVWKAMDRRTGEVVAIKKIFDAFR 50
       ||  ||  : .|||::|.||.||||||||||.||||||||||||||||||
     1 MCTV.VDPRIVRRYLLRRQLGQGAYGIVWKAVDRRTGEVVAIKKIFDAFR 49

51 DQTDAQRTFREIMLLREFGGHPNIIRLLDVIPAKNDRDIYLVFESMDTDL 100
       |.|||||||||| ||.||| ||||| ||||| |.||||||||||| |||||
    50 DKTDAQRTFREITLLQEFGDHPNIISLLDVIRAENDRDIYLVFEFMDTDL 99

101 NAVIQKGRLLEDIHKRCIFYQLLRATKFIHSGRVIHRDQKPANVLLDAAC 150
       ||||.|| ||:|:| | ||||||||:|:||| |:||||||.|||||| |
   100 NAVIRKGGLLQDVHVRSIFYQLLRATRFLHSGHVVHRDQKPSNVLLDANC 149

151 RVKLCDFGLARSLSDFPEG.LGQALTEYVATRWYRAPEVLLSSRWYTPGV 199
       |||||||||||| | |||  ||.||||||||||||||||||| || ||
   150 TVKLCDFGLARSLGDLPEGPEDQAVTEYVATRWYRAPEVLLSSHRYTLGV 199

200 DMWSLGCILGEMLRGQPLFPGTSTFHQLELILETIPLPSMEELQGLGSDY 249
       || 1 | |:.| |  ||   ||||  :  | || || ||  :
   200 DMRGLATIQGQILPGGQAQPGPPRQHQLEHTIXRTPXPSEEEHLGRGPGF 249

250 SALILQNLGSRPRQTLDALLPPDTPPEALDLLKRLLAFAPDKRLSAEQAL 299
       ||      ||||||||||||| |||||||:||| ||||||||| |||
   250 RPCILHTPAHRPRQTLDALLPPDTSPEALDLLRRLLVFAPDKRLSATQAL 299
```

Figure 3B

```
300 QHPYVQRFHCPDREWTRGSDVRLPVHEGDQLSAPEYRNRLYQMILERRRN 349
    ||||||||||| || | -|||   ||| ||| ||||-|-||||||   ·
300 QHPYVQRFHCPSDEWAREADVRPRAHEGVQLSVPEYRSRVYQMILECGGS 349

350 SRSPREEDLGVVASRAELRASQRQSLKPGVLPQVLAETPARKRGPKPQNG 399
    | . ||·  |·         ||    ||   ||- · || -   |:||·
350 SGTSREKGPEGVS......PSQAHLHKPRADPQLPSRTPVQGPRPRPQSS 393

400 HGHDPEHVE.......VRRQSSDPLYQLPPPGSGERPPGATGEPPSAPSG 442
    ||||    |       | ||-| || |   |-||||||||  ||    |
394 PGHDPAEHESPRAAKNVPRQNSAPLLQTALLGNGERPPGAKEAPPLTLSL 443

443 VKTHVRAVAPSLTSQAAAQAANQPLIRSDPARGGGPRAVGARRVPSRLPR 492
    ||  |  ||||||||||| |||  ||| |  |||| |        :|| |||
444 VKPSGRGAAPSLTSQAAAQVANQALIRGDWNRGGGVRVASXNKVPPRLP. 492

493 EAPEPRPGRRMFGISVSQGAQGAARAALGGYSQAYGTVCRSALGRLPLLP 542
    ||  |||||||  |    |||||  ||| ||||||||||||| |||| ||||
493 ..PEARPGRRMFSTSALQGAQGGARALLGGYSQAYGTVCHSALGHLPLLE 540

543 GPRA.  546
    |
541 Ghhv*  545
```

14189, A NOVEL HUMAN KINASE AND USES THEREOF

FIELD OF THE INVENTION

The invention relates to novel human kinase nucleic acid sequences and the encoded protein molecules. Also provided are vectors, host cells, and recombinant methods for making and using the novel molecules.

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786–791; Birchmeier et al. (1993) *Bioessays* 15:185–189). For example, these kinases have been shown to participate in the transmission of signals from growth-factor receptors (Sturgill et al. (1988) *Nature* 344:715–718; Gomez et al. (1991) *Nature* 353:170–173), control of entry of cells into mitosis (Nurse (1990) *Nature* 344:503–508; Mailer (1991) *Curr. Opin. Cell Biol.* 3:269–275), and regulation of actin bundling (Husain-Chishti et al. (1988) *Nature* 334:718–721). Protein kinases serve as growth factor receptors and signal transducers and have been implicated in cellular transformation and malignancy (Hunter et al. (1992) *Cell* 70:375–387; Posada et al. (1992) *Mol. Biol. Cell* 3:583–592; Hunter et al. (1994) *Cell* 79:573–582). Alterations in kinase genes and their products can lead to deregulated cell proliferation, a hallmark of cancer. Modulation of these genes and their regulatory activities may permit the control of tumor cell proliferation and invasion.

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) *Science* 241:42–52).

Extracellular signal-regulated kinases/mitogen-activated protein kinases (ERKs\MAPKs) and cyclin-directed kinases (Cdks) represent two large families of serine-threonine kinases (see Songyang et al. (1996) *Mol. Cell. Biol.* 16: 6486–6493). Both types of kinases function in cell growth, cell division, and cell differentiation in response to extracellular stimuli. The ERK\MAPK family members are critical participants in intracellular signaling pathways. Upstream activators as well as the ERK\MAPK components are phosphorylated following contact of cells with growth factors or hormones or in response to cellular stressors, for example, heat, ultraviolet light, and inflammatory cytokines. These kinases transport messages that have been relayed from the plasma membrane to the cytoplasm by upstream kinases into the nucleus where they phosphorylate transcription factors and effect gene transcription modulation (Karin et al. (1995) *Curr. Biol.* 5: 747–757). Substrates of the ERK\MAPK family include c-fos, c-jun, APF2, and ETS family members Elk1, Sap1a, and c-Ets-1 (cited in Brott et al. (1998) *Proc. Natl. Acad. Sci. USA* 95: 963–968).

Signal-transduction pathways that employ members of the ERK/MAPK family of serine/threonine kinases are widely conserved among eukaryotes. The multiplicity of these pathways allows the cell to respond to divergent extracellular stimuli by initiating a broad array of responses ranging from cell growth to apoptosis. ERK/MAPK pathways are comprised of a three-tiered core-signaling module wherein ERK/MAPKs are regulated by MAPK/ERK kinases (MEKs), and MEKs, in turn, are regulated by MAPK kinase kinases (MAPKKKs). Mammalian stress-activated ERK/MAPK pathways have been implicated in numerous important physiological functions, including cell growth and proliferation, inflammatory responses, and apoptosis. For example, activation of the ERK 1,2 signaling pathway by a mitogenic growth factor, a tumor promoter, or by transformation suppresses decorin gene expression in fibroblasts, which in turn may promote proliferation and migration of normal and malignant cells (Laine et al. (2000) *Biochem. J.* 349: 19–25).

Cdks regulate transitions between successive stages of the cell cycle. The activity of these molecules is controlled by phosphorylation events and by association with cyclin. Cdk activity is negatively regulated by the association of small inhibitory molecules (Dynlacht (1997) *Nature* 389:148–152). Cdk targets include various transcriptional activators such as p110Rb, p107, and transcription factors, such as p53, E2F, and RNA polymerase II, as well as various cytoskeletal proteins and cytoplasmic signaling proteins (cited in Brott et al. (1998) *Proc. Natl. Acad. Sci. USA* 95: 963–968).

Protein kinases play critical roles in cellular growth, particularly in the transduction of signals for cell proliferation, differentiation, and apoptosis. Therefore, novel protein kinase polynucleotides and proteins are useful for modulating cellular growth, differentiation, and/or development.

SUMMARY OF THE INVENTION

Isolated nucleic acid molecules corresponding to kinase nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequence encoding the DNA sequence deposited in a plasmid vector as ATCC Accession Number PTA 2333. Further provided are kinase polypeptides having amino acid sequences encoded by the nucleic acid molecules described herein.

The present invention also provides vectors and host cells for recombinant expression of the nucleic acid molecules described herein, as well as methods of making such vectors and host cells and for using them for production of the polypeptides or peptides of the invention by recombinant techniques.

The kinase molecules of the present invention are useful for modulating cellular growth, cellular proliferation, and/or cellular metabolic pathways, particularly for regulating one or more proteins involved in growth, proliferation, and metabolism. Accordingly, in one aspect, this invention provides isolated nucleic acid molecules encoding kinase proteins or biologically active portions thereof, as well as nucleic acid fragments suitable as primers or hybridization probes for the detection of kinase-encoding nucleic acids.

Another aspect of this invention features isolated or recombinant kinase proteins and polypeptides. Preferred kinase proteins and polypeptides possess at least one biological activity possessed by the naturally occurring kinase proteins of the invention.

Variant nucleic acid molecules and polypeptides substantially homologous to the nucleotide and amino acid sequences of the present invention are encompassed. Additionally, fragments and substantially homologous fragments of the nucleotide and amino acid sequences of the present invention are provided.

Antibodies and antibody fragments that selectively bind the kinase polypeptides and fragments thereof are provided. Such antibodies are useful in detecting the kinase polypeptides as well as in modulating cellular growth, proliferation, and metabolism.

In another aspect, the present invention provides a method for detecting the presence of kinase activity or expression in a biological sample by contacting the biological sample with an agent capable of detecting an indicator of kinase activity such that the presence of kinase activity is detected in the biological sample.

In yet another aspect, the invention provides a method for modulating kinase activity comprising contacting a cell with an agent that modulates (inhibits or stimulates) kinase activity or expression such that kinase activity or expression in the cell is modulated. In one embodiment, the agent is an antibody that specifically binds to kinase protein. In another embodiment, the agent modulates expression of kinase protein by modulating transcription of a kinase gene, splicing of a kinase mRNA, or translation of a kinase mRNA. In yet another embodiment, the agent is a nucleic acid molecule having a nucleotide sequence that is antisense to the coding strand, or to a portion thereof, of the kinase MRNA or the kinase gene.

In one embodiment, the methods of the present invention are used to treat a subject having a disorder characterized by the aberrant activity or nucleic acid expression of the kinase proteins of the invention by administering an agent that is a kinase modulator to the subject. In one embodiment, the kinase modulator is a kinase protein. In another embodiment, the kinase modulator is a kinase nucleic acid molecule. In other embodiments, the kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of the gene encoding a kinase protein of the invention; (2) misregulation of the gene encoding a kinase protein of the invention; and (3) aberrant post-translational modification of a kinase protein of the invention, wherein the wild-type form of the gene encodes a protein with kinase activity.

In another aspect, the invention provides a method for identifying a compound that binds to or modulates the activity of a kinase protein of the invention. In general, such methods entail measuring a biological activity of the kinase protein in the presence and absence of a test compound and identifying those compounds that alter the activity of the kinase protein.

The invention also features methods for identifying a compound that modulates the expression of a kinase gene of the invention by measuring the expression of the kinase sequence in the presence and absence of the compound.

Other features and advantages of the invention will be apparent from the following detailed description and claims.

BRIEF DESCRIPTION OF THE DRAWINGS

FIGS. 1A and 1B provide the nucleotide (SEQ ID NO:1) and amino acid sequence (SEQ ID NO:2) for the novel human protein kinase of the invention, h14189.

FIGS. 2A–D show a nucleotide sequence alignment of the open reading frame of h14189 (SEQ ID NO:1) with nucleotides 151-1804 of the rat extracellular signal-regulated kinase 7, ERK7 (Accession Number AF078798; SEQ ID NO:3). These sequences display approximately 77% identity.

FIGS. 3A and 3B show an amino acid sequence alignment h14189 (SEQ ID NO:2) with rat extracellular signal-regulated kinase 7, ERK7 (Accession Number 4220888; SEQ ID NO:4). These sequences display 66.6% identity and 69.2% similarity.

DETAILED DESCRIPTION OF THE INVENTION

Figure 4A:
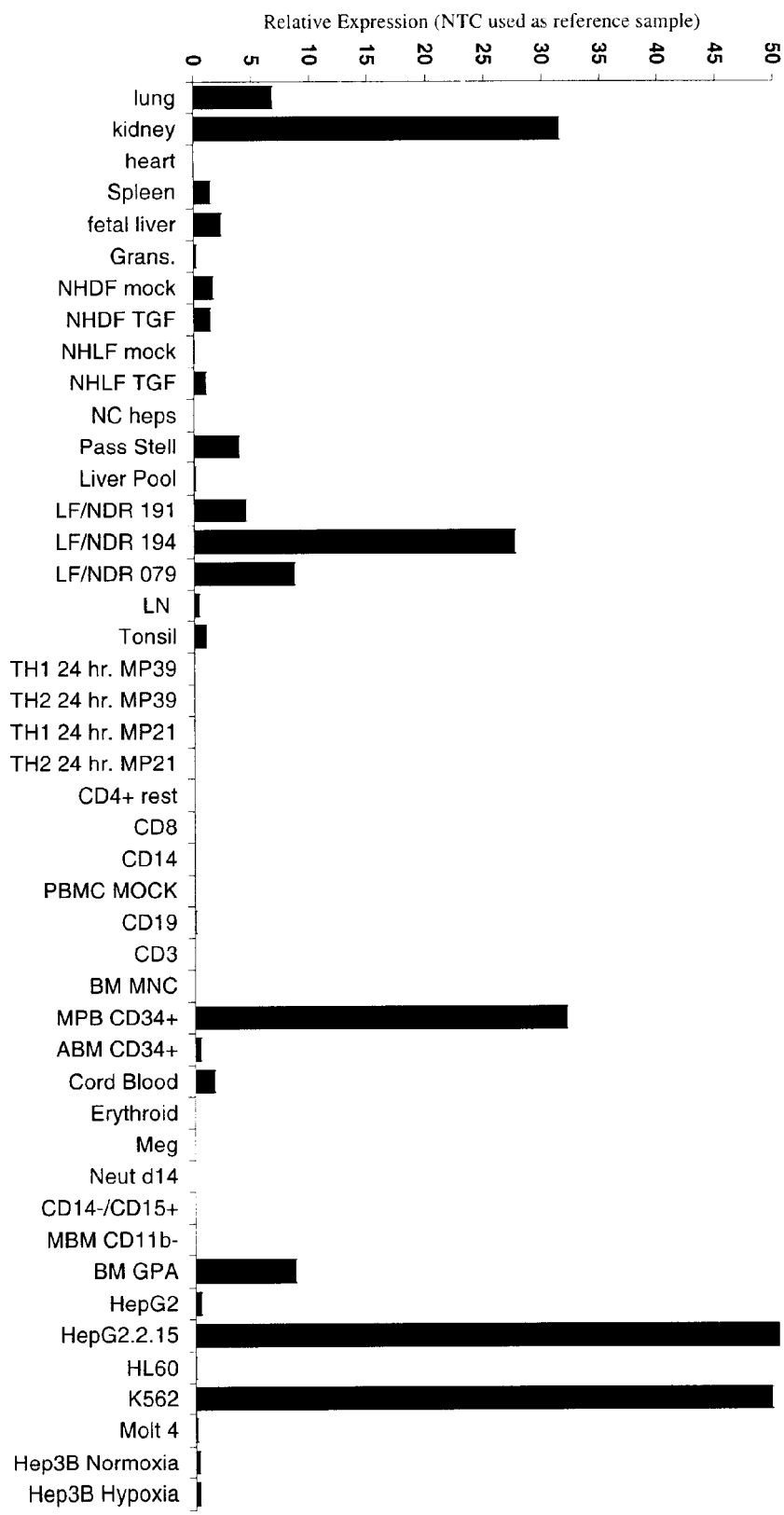
FIGS. 4A and 4B show h14189 gene expression determined by TaqMan® quantitative PCR in various tissues and cell types. The highest levels of h14189 expression were observed in normal kidney and lung tissue, HepG2 cells transfected with HBV (HepG2.2.15), fibrotic liver samples (NF/NDR), a transformed human erythroleukemia cell line (K562), and cells from mobilized peripheral blood (MPB CD34$^+$). Significant levels of h14189 expression were also observed in human hepatic stellate cells, spleen, tonsil, cord blood, bone marrow, and dermal fibroblasts.
Figure 4B:
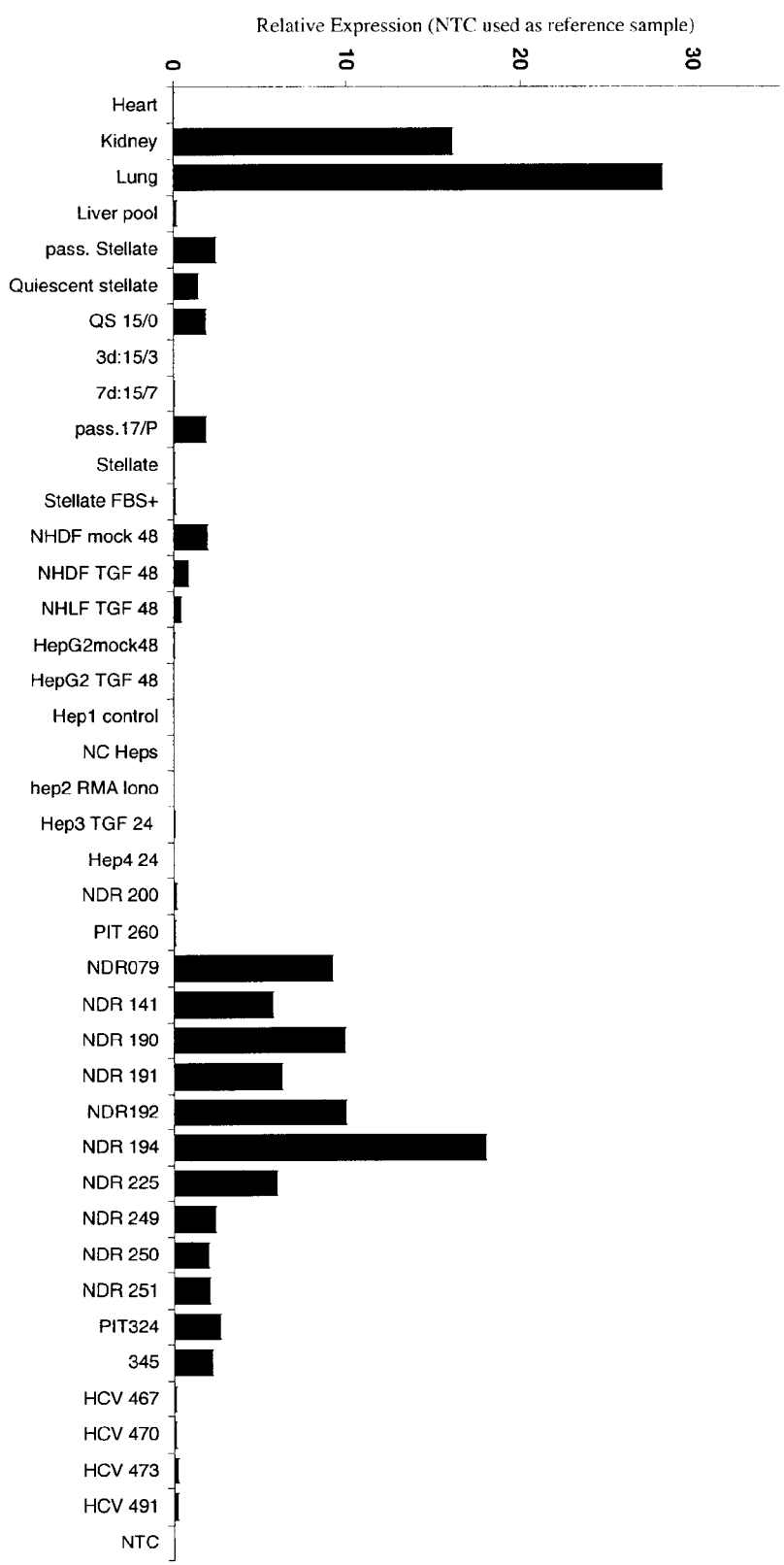

The present invention is based, at least in part, on the discovery of novel molecules, referred to herein as "kinase" nucleic acid and polypeptide molecules, which play a role in, or function in, signaling pathways associated with cellular growth, cellular proliferation, differentiation and/or cellular metabolic pathways. These growth, proliferation, and metabolic pathways are described in Lodish et al. (1995) *Molecular Cell Biology* (Scientific American Books Inc., New York, N.Y.) and Stryer Biochemistry (W. H. Freeman, NY), the contents of which are incorporated herein by reference. In one embodiment, the kinase molecules of the invention modulate the activity of one or more proteins involved in cellular growth or differentiation, e.g., cardiac, hepatic stellate, or dermal fibroblast cell growth or differentiation. In another embodiment, the kinase molecules of the present invention are capable of modulating the phosphorylation state of a kinase molecule or the phosphorylation state of one or more proteins involved in cellular growth or differentiation, e.g., cardiac, hepatic stellate, or dermal fibroblast cell growth or differentiation, as described in, for example, Lodish et al. and Stryer, supra. In addition, the kinases of the present invention are a target of drugs described in Goodman and Gilman (1996) *The Pharmacological Basis of Therapeutics* ($9^{th}$ ed.), ed. Hartman and Limbard, the contents of which are incorporated herein by reference. Particularly, the kinases of the present invention may modulate phosphorylation of cellular proteins and proteinaceous molecules in tissues and cells including, but not limited to, lung; kidney; spleen; fetal liver; normal liver; fibrotic liver; lymph nodes; tonsil; HepG2 cells; Hep3 cells; granulocytes; dermal and lung fibroblasts; hepataic stellate cells; CD8+ T cells; T-cells; CD19+ B cells; CD34+ cells from mobilized peripheral blood; adult resting bone marrow; GPA+ cells from bone marrow, cord blood; hepatitic-C virus-infected liver (HCV); and the transformed erythroleukemia cell lines as shown in FIGS. 4A and 4B.

As used herein, the term "kinase" includes a protein, polypeptide, or other non-proteinaceous molecule that is capable of modulating its own phosphorylation state or the phosphorylation state of a different protein, polypeptide, or other non-proteinaceous molecule. Kinases can have a specificity for (i.e., a specificity to phosphorylate) serine/threonine residues, tyrosine residues, or both serine/threonine and tyrosine residues, e.g., the dual-specificity kinases. As referred to herein, kinases such as protein kinases preferably include a catalytic domain of about 200–400 amino acid residues in length, preferably about 200–300 amino acid residues in length, or more preferably about 250–300 amino acid residues in length, which includes preferably 5–20, more preferably 5–15, or most preferably 11 highly conserved amino acids separated by sequences of amino acids with reduced or minimal conservation referred to herein as subdomains or motifs. Specificity of a kinase for phosphorylation of either tyrosine or serine/threonine can be predicted by the sequence of two of the subdomains (VIb and VIII) in which different residues are conserved in each class (as described in, for example, Hanks et al. (1988) Science 241:42–52, the contents of which are incorporated herein by reference). These subdomains are also described in further detail herein.

The novel kinase protein and nucleic acid molecules of the present invention belong to a family of molecules having certain conserved structural and functional features. The term "family" when referred to herein is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features kinase nucleic acid molecules, preferably human kinase nucleic acid molecules that were identified based on a consensus motif or protein domain characteristic of a kinase family of proteins. Specifically, the novel human gene, termed clone h14189,is provided (SEQ ID NO:1; FIGS. 1A and 1B), as well as variants and fragments thereof. Such sequences are referred to as "kinase" sequences indicating that the open reading frames share sequence similarity with those of kinase genes.

The isolated nucleic acid molecules of the present invention encode a eukaryotic protein kinase polypeptide (SEQ ID NO:2; FIG. 1), or variants thereof, that reside within the eukaryotic protein kinase family. Eukaryotic protein kinases (described in, for example, Hanks et al. (1995) FASEB J. 9:576–596) are enzymes that belong to an extensive family of proteins that share a conserved catalytic core or domain common to both serine/threonine and tyrosine protein kinases. There are a number of conserved regions in the catalytic core or domain of protein kinases. One of these regions, located in the N-terminal extremity of the catalytic domain, is a glycine-rich stretch of residues in the vicinity of a lysine residue, which has been shown to be involved in ATP binding. A consensus sequence (SEQ ID NO:11) for this region is:

[LIV]-G-{P}-G-{P}-[FYWMGSTNH]-[SGA]-{PW}-[LIVCAT]-{PD}-x-[GSTACLIVMFY]-x(5, 18)-[LIVMFYWCSTAR]-[AIVP]-[LIVMFAGCKR]-K [K BINDS ATP]

In this and the following consensus sequence patterns, each element in the pattern is separated by a dash (-); square [ ] parentheses indicate the particular residues that are accepted at that position; curly { } brackets indicate the residues that are not accepted at that position; x indicates any residue is accepted at that position; repetition of a particular element is indicated by following the element with a numerical value or a numerical range enclosed in parentheses (i.e., above, x(5,18) indicates anywhere from 5–18 residues are present in the element, and any residue can be accepted at each of these 5–18 residue positions); and the standard IUPAC one-letter code for the amino acids is used. In the h14189 polypeptide set forth in SEQ ID NO:2, this ATP binding region resides at amino acids 19–42 (see FIG. 1). The K residue at position 29 and/or 42 can be involved in ATP binding.

Another region, located in the central part of the catalytic core or domain, contains a conserved aspartic acid residue, which is important for the catalytic activity of the enzyme (Knighton et al. (1991) Science 253:407–414). Two signature patterns have been described for this region: one specific for serine/threonine kinases and one for tyrosine kinases. A consensus sequence for the serine/threonine kinases (SEQ ID NO:12) is:

[LIVMFYC]-x-[HY]-x-D-[LIVMFY]-K-x(2)-N-[LIVMFYCT](3)

D Is an Active Site Residue

A consensus sequence for the tyrosine kinases (SEQ ID NO:13) is:

[LIVMFYC]-x-[HY]-x-D-[LIVMFY]-[RSTAC]-x(2)-N-[LIVMFYC](3)

D Is an Active Site Residue

The signature pattern for the h14189 polypeptide of the present invention most resembles that of a serine/threonine kinase and resides at amino acids 133–145 (see FIG. 1).

The kinase molecules of the present invention were discovered based on a novel cDNA sequence identified in a lung tissue library. This clone, h14189, encodes an approximately 1.9 kb mRNA transcript having the corresponding cDNA sequence set forth in SEQ ID NO:1 (see FIG. 1). This transcript has a 1635 nucleotide open reading frame including the stop codon (nucleotides 48–1682 of SEQ ID NO: 1), which encodes a 544 amino acid protein (SEQ ID NO:2) having a molecular weight of approximately 59.83 kDa. The molecule does not appear to contain a transmembrane segment as predicted by MEMSAT.

Prosite program analysis was used to predict various sites within the h14189 protein. An N-glycosylation site was predicted at amino acids (aa) 148–151. A glycosaminoglycan attachment site was predicted at aa 447–450. A cAMP- and cGMP-dependent protein kinase phosphorylation site was predicted at aa 291–294. Protein kinase C phosphorylation sites were predicted at aa 57–59, 150–152, 192–194, 352–354, 403–405, and 447–449. Casein kinase II phosphorylation sites were predicted at aa 3–6, 57–60, 75–78, 161–164, 238–241, 273–276, 331–334, and 352–355. A tyrosine phosphorylation site was predicted at aa 81–89. N-myristoylation sites were predicted at aa 157–162, 327–332, 347–352, 360–365, 450–455, 478–483, and 509–514. An amidation site was predicted at aa 497–500, and an RGD cell attachment sequence was predicted at aa 470–472. A protein kinase signature ATP-binding region was predicted at aa 19–42.

The h14189 protein possesses two porfiens of the eukaryotic protin kinase domains, the first spanning aa 13–201 and the second at aa 269–304, as predicted by HMMer, Version 2. A serine kinase domain and a tyrosine kinase domain were also predicted for the h14189 protein by HMMer analysis, spanning aa 13–304 and aa 13–307, respectively. However, there is a much higher degree of similarity between h14189 and the consensus serine kinase domain (score of 278.4 and E-value of $9.5\ e^{-80}$) than between this protein and the consensus tyrosine kinase domain (score of 19.7 and E value of $4\ e^{-13}$). Further, the h14189 signature pattern, VVHRDQKPSNVLL (aa residues 133–145 of FIG. 1 and SEQ ID NO:2), matches more closely with the consensus sequence for the serine/threonine kinases (shown above), than with that of the tyrosine kinases (shown above).

BLAST analysis of the patent and public nucleic acid and protein databases indicates that the h14189 protein kinase shares the most similarity with several extracellular signal-regulated protein kinases (ERKs) and mitogen activated protein kinases (MAPKs). The h14189 protein kinase displays the closest homology with a rat protein known as ERK7 kinase (Accession Number AF078798; SEQ ID NO:4). GAP analysis of the open reading frames of the cDNAs encoding the h14189 kinase protein of the invention and the rat ERK7 kinase (Accession Number AF078798) shows that these nucleotide sequences share approximately 77.2% identity (see FIGS. 2A–D). GAP analysis of the h14189 kinase protein of the invention and the rat ERK7 kinase protein (Accession Number 4220888) demonstrates that these proteins share approximately 66.6% identity (see FIGS. 3A and 3B).

A plasmid containing the human kinase 14189 cDNA insert was deposited with American Type Culture Collection (ATCC), 10801 University Boulevard, Manassas, Va. on Aug. 3, 2000, and assigned Accession Number PTA-2333. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Preferred kinase polypeptides of the present invention have an amino acid sequence sufficiently identical to the amino acid sequence of SEQ ID NO:2, or a domain thereof. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain (e g., a eukaryotic kinase domain, serine kinase domain, and/or tyrosine kinase domain) and/or common functional activity. For example, amino acid or nucleotide sequences that contain a common structural domain having at least about 80% identity, preferably 85% identity, more preferably 90%, and most preferably 91%, 92%, 93%, 94%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the kinase nucleic acid molecule of the invention. BLAST protein searches can be performed with the XBLAST program, score=50, wordlength=3, to obtain amino acid sequences homologous to the kinase protein molecule of the invention. To obtain gapped alignments for comparison purposes, Gapped BLAST can be utilized as described in Altschul et al. (1997) *Nucleic Acids Res.* 25:3389. Alternatively, PSI-BLAST can be used to perform an iterated search that detects distant relationships between molecules. When utilizing BLAST, Gapped BLAST, and PSI-BLAST programs, the default parameters of the respective programs (e.g., XBLAST and NBLAST) can be used. See http://www.ncbi.nlm.nih.gov. Another preferred, example of an algorithm utilized for the comparison of sequences is the algorithm of Myers and Miller (1988) *CABIOS* 4:11–17. Such an algorithm is incorporated into the ALIGN program (version 2.0), which is part of the GCG sequence alignment software package. When utilizing the ALIGN program for comparing amino acid sequences, a PAM 120 weight residue table, a gap length penalty of 12, and a gap penalty of 4 can be used. A preferred program is the Pairwise Alignment Program (Sequence Explorer), using default parameters.

Accordingly, another embodiment of the invention features isolated kinase protein and polypeptides having a kinase protein activity. As used interchangeably herein, a "kinase protein activity", "biological activity of a kinase protein", or "functional activity of a kinase protein" refers to an activity exerted by a kinase protein, polypeptide, or nucleic acid molecule on a kinase-responsive cell as determined in vivo, or in vitro, according to standard assay techniques. A kinase activity can be a direct activity, such as an association with or an enzymatic activity on a second protein, or an indirect activity, such as a cellular signaling activity mediated by interaction of the kinase protein with a second protein. In one embodiment, a kinase activity includes at least one or more of the following activities: (1) modulating (stimulating and/or enhancing or inhibiting) cellular proliferation, growth and/or metabolism (e.g. in those cells in which the sequence is expressed, including, lung; kidney; spleen; fetal liver, normal liver, and fibrotic liver, lymph nodes, and tonsil; HepG2 cells; HepG2 cells transfected with HBV; Hep3 cells; granulocytes; dermal and lung fibroblasts; hepatic stellate cells; $CD8^+$ T cells; T-cells;

CD19+ B cells; CD34+ cells from mobilized peripheral blood; adult resting bone marrow; GPA+ cells from bone marrow, cord blood; hepatitic-C virus-infected liver (HCV); and the transformed erythroleukemia cell lines); (2) the regulation of transmission of signals from cellular receptors, including growth factor receptors; (3) the modulation of the entry of cells into mitosis; (4) the modulation of cellular differentiation; (5) the modulation of cell death; and (6) the regulation of cytoskeleton function including actin bundling.

Assays for measuring kinase activity are well known in the art depending on the particular kinase. Specific assay protocols are available in standard sources known to the ordinarily skilled artisan. For example, see "Kinases" in Ausubel et al., eds. (1994–1998) *Current Protocols in Molecular Biology* (3) and references cited therein.

An "isolated" or "purified" kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A kinase protein that is substantially free of cellular material includes preparations of kinase protein having less than about 30%, 20%, 10%, or 5% (by dry weight) of non-kinase protein (also referred to herein as a "contaminating protein"). When the kinase protein or biologically active portion thereof is recombinantly produced, preferably, culture medium represents less than about 30%, 20%, 10%, or 5% of the volume of the protein preparation. When kinase protein is produced by chemical synthesis, preferably the protein preparations have less than about 30%, 20%, 10%, or 5% (by dry weight) of chemical precursors or non-kinase chemicals.

Kinases play a role in signaling pathways associated with cellular growth. For example, protein kinases are involved in the regulation of signal transmission from cellular receptors such as growth-factor receptors, entry of cells into mitosis, and the regulation of cytoskeleton function. Signal-transduction pathways that employ members of the ERK/MAPK family of protein serine/threonine kinases are widely conserved among eukaryotes. As previously noted, mammalian stress-activated ERK/MAPK pathways have been implicated in numerous important physiological functions, including cell growth and proliferation, inflammatory responses, and apoptosis.

Inhibition or over stimulation of the activity of kinases involved in signaling pathways associated with cellular growth can lead to perturbed cellular growth, which can in turn lead to cellular growth-related disorders. As used herein, a "cellular growth-related disorder" includes a disorder, disease, or condition characterized by a deregulation, e.g., an up-regulation or a down-regulation, of cellular growth. Cellular growth deregulation may be due to a deregulation of cellular proliferation, cell cycle progression, cellular differentiation and/or cellular hypertrophy. Examples of such cellular growth-related disorders include, but are not limited to, cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma. The compositions of the invention are useful in the diagnosis and/or treatment of such disorders, as well as of liver fibrosis and other liver-related disorders. Disorders associated with the following cells or tissues are also encompassed: lung; kidney; spleen; fetal liver, normal liver, and fibrotic liver, lymph nodes, and tonsil; HepG2 cells; granulocytes; dermal and lung fibroblasts; hepatic stellate cells; CD8+ T cells; T-cells; CD19+ B cells; CD34+ cells from mobilized peripheral blood; bone marrow; and cord blood.

In view of the biological function of the kinase molecules of the invention, these molecules and modulators thereof can be used in methods of the invention directed to the modulation, diagnosis, and treatment of disorders, including, but not limited to, liver disorders, fibrotic disorders, and immune, inflammatory, respiratory, and hematological disorders. Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografs; tumors and tumorous conditions, such as nodular hyperplasias, adenomas, and malignant tumors, including primary carcinoma of the liver and metastatic tumors.

Fibrotic disorders or diseases include fibrosis in general, e.g., chronic pulmonary obstructive disease; ideopathic pulmonary fibrosis; crescentic glomerulofibrosis; sarcoidosis; cystic fibrosis; fibrosis/cirrhosis, including cirrhosis secondary to chronic alcoholism, cirrhosis secondary to hepatitis type B or hepatitis type C, and primary biliary cirrhosis; liver disorders disclosed above, particularly liver fibrosis; and other fibrotic diseases; as well as fibrosis associated with the treatment of bums and scarring.

Immune disorders include, but are not limited to, chronic inflammatory diseases and disorders, inflammatory bowel diseases such as Crohn's disease and ulcerative colitis, rheumatoid arthritis, including Lyme disease, insulindependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Respiratory disorders include, but are not limited to, apnea, asthma, particularly bronchial asthma, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Hematologic disorders include but are not limited to anemias including sickle cell and hemolytic anemia, hemophilias including types A and B, leukemias, thalassemias, spherocytosis, Von Willebrand disease, chronic granulomatous disease, glucose-6-phosphate dehydrogenase deficiency, thrombosis, clotting factor abnormalities and deficiencies including factor VIII and IX deficiencies, hemarthrosis, hematemesis, hematomas, hematuria, hemochromatosis, hemoglobinuria, hemolytic-uremic syndrome, thrombocytopenias including HIV-associated thrombocytopenia, hemorrhagic telangiectasia, idiopathic thrombocytopenic purpura, thrombotic microangiopathy, hemosiderosis.

Various aspects of the invention are described in further detail in the following subsections.

I. Isolated Nucleic Acid Molecules

One aspect of the invention pertains to isolated nucleic acid molecules comprising nucleotide sequences encoding the kinase proteins of the present invention or biologically active portions thereof, as well as nucleic acid molecules sufficient for use as hybridization probes to identify kinase-encoding nucleic acids (e.g., kinase mRNA) and fragments for use as PCR primers for the amplification or mutation of kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the kinase proteins of the present invention include the sequence set forth in SEQ ID NO:1, the nucleotide sequence of the cDNA insert of the plasmid deposited with the ATCC as Accession Number PTA-2333 (referred to as the "cDNA of ATCC PTA-2333"), and complements thereof. By "complement" is intended a nucleotide sequence that is sufficiently complementary to a given nucleotide sequence such that it can hybridize to the given nucleotide sequence to thereby form a stable duplex. The amino acid sequence of the kinase protein encoded by these nucleotide sequences is set forth in SEQ ID NO:2.

Nucleic acid molecules that are fragments of the kinase nucleotide sequences of the invention are also encompassed by the present invention. By "fragment" is intended a portion of the nucleotide sequence encoding a kinase protein of the invention. A fragment of a kinase nucleotide sequence may encode a biologically active portion of the kinase protein, or it may be a fragment that can be used as a hybridization probe or PCR primer using methods disclosed below. A biologically active portion of a kinase protein of the invention can be prepared by isolating a portion of one of the kinase nucleotide sequences of the invention, expressing the encoded portion of the kinase protein (e.g., by recombinant expression in vitro), and assessing the activity of the encoded portion of the kinase protein. Generally, nucleic acid molecules that are fragments of a kinase nucleotide sequence comprise at least 15, 20, 25, 30, 35, 40, 45, 50, 75, 100, 325, 350, 375, 400, 425, 450, 500, 600, 700, 800, 900, 1000, 1100, 1200, 1300, 1400, 1450, 1500, 1550, 1600, or 1620 nucleotides, or up to the number of nucleotides present in a full-length kinase nucleotide sequence disclosed herein (for example, 1635 nucleotides for SEQ ID NO:1) depending upon the intended use.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a kinase nucleotide sequence that encodes a biologically active portion of the kinase protein of the invention will encode at least 20, 25, 30, 50, 75, 100, 125, 150, 175, 200, 250, 300, 350, 400, 450, 475, 500, 525, 530, or 540 contiguous amino acids, or up to the total number of amino acids present in a full-length kinase protein of the invention (for example, 544 amino acids for SEQ ID NO:2). Fragments of a kinase nucleotide sequence that are useful as hybridization probes for PCR primers generally need not encode a biologically active portion of a kinase protein.

Nucleic acid molecules that are variants of the kinase nucleotide sequences disclosed herein are also encompassed by the present invention. "Variants" of the kinase nucleotide sequences include those sequences that encode the kinase proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically-derived nucleotide sequences that have been generated, for example, by using site-directed mutagenesis but which still encode the kinase proteins disclosed in the present invention as discussed below. Generally, nucleotide sequence variants of the invention will have at least about 80%, 85%, 90%, 91%, 92%, 93%, 94%, 95%, 96%, 97%, 98%, or 99% identity to the nucleotide sequences disclosed herein. A variant kinase nucleotide sequence will encode a kinase protein that has an amino acid sequence having at least about 70%, 75%, 80%, 85%, 90%, 91%, 92%, 93%, 94%, 95%, 96%, 97%, 98% or 99% identity to an amino acid sequence of a kinase protein disclosed herein.

In addition to the kinase nucleotide sequence shown in SEQ ID NO:1, and the nucleotide sequence of the cDNA of ATCC PTA-2333, it will be appreciated by those skilled in the art that DNA sequence polymorphisms that lead to changes in the amino acid sequences of kinase proteins may exist within a population (e.g., the human population). Such genetic polymorphism in a kinase gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a kinase protein, preferably a mammalian kinase protein. As used herein, the phrase "allelic variant" refers to a nucleotide sequence that occurs at a kinase locus or to a polypeptide encoded by the nucleotide sequence. Such natural allelic variations can typically result in 1–5% variance in the nucleotide sequence of the kinase gene. Any and all such nucleotide variations and resulting amino acid polymorphisms or variations in a kinase sequence that are the result of natural allelic variation and that do not alter the functional activity of kinase proteins are intended to be within the scope of the invention.

Moreover, nucleic acid molecules encoding kinase proteins from other species (kinase homologues), which have a nucleotide sequence differing from that of the kinase sequences disclosed herein, are intended to be within the scope of the invention. Nucleic acid molecules corresponding to natural allelic variants and homologues of the kinase cDNA of the invention can be isolated based on their identity to the human kinase nucleic acids disclosed herein using the human cDNAs, or a portion thereof, as a hybridization probe according to standard hybridization techniques under stringent hybridization conditions as disclosed below.

In addition to naturally occurring allelic variants of the kinase sequence that may exist in the population, the skilled artisan will further appreciate that changes can be introduced by mutation into the nucleotide sequences of the invention thereby leading to changes in the amino acid sequence of the encoded kinase protein, without altering the biological activity of the kinase protein. Thus, an isolated nucleic acid molecule encoding a kinase protein having a sequence that differs from that of SEQ ID NO:2 can be created by introducing one or more nucleotide substitutions, additions, or deletions into the nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a kinase protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues or for amino acid residues residing within a conserved protein domain, such as the critical eukaryotic protein kinase domain of the disclosed clone, where such residues are essential for protein activity.

Alternatively, variant kinase nucleotide sequences can be made by introducing mutations randomly along all or part of a kinase coding sequence, such as by saturation mutagenesis, and the resultant mutants can be screened for kinase biological activity to identify mutants that retain activity. Following mutagenesis, the encoded protein can be expressed recombinantly, and the activity of the protein can be determined using standard assay techniques.

Thus the nucleotide sequences of the invention include SEQ ID NO:1 and the nucleotide sequence of the cDNA of ATCC PTA-2333, as well as fragments and variants thereof. The kinase nucleotide sequences of the invention, and fragments and variants thereof, can be used as probes and/or primers to identify and/or clone kinase homologues in other cell types, e.g., from other tissues, as well as kinase homologues from other mammals. Such probes can be used to detect transcripts or genomic sequences encoding the same or identical proteins. These probes can be used as part of a diagnostic test kit for identifying cells or tissues that display aberrant expression of a kinase protein of the invention, such as by measuring levels of a kinase-encoding nucleic acid in a sample of cells from a subject, e.g., detecting kinase mRNA levels or determining whether a genomic kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Kinase nucleotide sequences isolated based on their sequence identity to the kinase nucleotide sequences set forth herein or to fragments and variants thereof are encompassed by the present invention.

In a hybridization method, all or part of a known kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known kinase nucleotide sequences disclosed herein. Degenerate primers designed on the basis of conserved nucleotides or amino acid residues in a known kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of the kinase nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified kinase nucleic acid molecule hybridizes under stringent conditions to a probe that is a nucleic acid molecule comprising the kinase nucleotide sequence of the invention or a fragment thereof. In another embodiment, the previously unknown kinase nucleic acid molecule is at least 300, 325, 350, 375, 400, 425, 450, 500, 550, 600, 650, 700, 800, 900, 1000, 2,000, 3,000, or 4,000 nucleotides in length and hybridizes under stringent conditions to a probe that is a nucleic acid molecule comprising the kinase nucleotide sequence disclosed herein or a fragment thereof.

Accordingly, in another embodiment, an isolated previously unknown kinase nucleic acid molecule of the invention is at least 300, 325, 350, 375, 400, 425, 450, 500, 518, 550, 600, 650, 700, 800, 831, 900, 981, 1000, 1,100, 1,200, 1,300, 1,400, 1,500, 1,600, 1,700, 1,800, 1,900, 2,000, or 2,060 nucleotides in length and hybridizes under stringent conditions to a probe that is a nucleic acid molecule comprising the nucleotide sequence of SEQ ID NO:1, the cDNA of ATCC PTA-2333, or a complement, fragment, or variant thereof.

As used herein, the term "hybridizes under stringent conditions" is intended to describe conditions for hybridization and washing under which nucleotide sequences having at least 60%, 65%, 70%, preferably 75% or more identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization conditions is hybridization in 6×sodium chloride/sodium citrate (SSC) at about 45° C., followed by one or more washes in 0.2×SSC, 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to a kinase sequence of the invention corresponds to a naturally occurring nucleic acid molecule. As used herein, a "naturally occurring" nucleic acid molecule refers to an RNA or DNA molecule having a nucleotide sequence that occurs in nature (e.g., encodes a natural protein).

Thus, in addition to the kinase nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the kinase nucleotide sequence disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase coding strand, or to only a portion thereof, e.g., all or part of the protein coding region (or open reading frame). An antisense nucleic acid molecule can be antisense to a noncoding region of the coding strand of a nucleotide sequence encoding a kinase protein. The noncoding regions are the 5' and 3' sequences that flank the coding region and are not translated into amino acids.

Given the coding-strand sequence encoding the kinase protein disclosed herein (e.g., SEQ ID NO:1), antisense nucleic acids of the invention can be designed according to the rules of Watson and Crick base pairing. The antisense nucleic acid molecule can be complementary to the entire coding region of kinase mRNA, but more preferably is an oligonucleotide that is antisense to only a portion of the coding or noncoding region of kinase mRNA. For example, the antisense oligonucleotide can be complementary to the region surrounding the translation start site of kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example, phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject or generated in situ such that they hybridize with or bind to cellular mRNA and/or genomic DNA encoding a kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave kinase mRNA transcripts to thereby inhibit translation of kinase mRNA. A ribozyme having specificity for a kinase-encoding nucleic acid can be designed based upon the nucleotide sequence of the kinase cDNA disclosed herein (e.g., SEQ ID NO:1). See, e.g., Cech et al., U.S. Pat. No. 4,987,071; and Cech et al., U.S. Pat. No. 5,116,742. Alternatively, kinase mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, kinase gene expression can be inhibited by targeting nucleotide sequences complementary to the regulatory region of the kinase protein (e.g., the kinase promoter and/or enhancers) to form triple helical structures that prevent transcription of the kinase gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In other embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a kinase molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping, as artificial restriction enzymes when used in combination with other enzymes, e.g., S1 nucleases (Hyrup (1996), supra, or as probes or primers for DNA sequence and hybridization (Hyrup (1996), supra; Perry-O'Keefe et al. (1996), supra).

In another embodiment, PNAs of a kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63;Mag et al. (1989) *Nucleic Acids Res.* 17:5973; and Peterser et al. (1975) *Bioorganic Med. Chem. Lett.* 5:1119.

II. Isolated Kinase Proteins and Anti-kinase Antibodies

Kinase proteins are also encompassed within the present invention. By "kinase protein" is intended proteins having the amino acid sequence set forth in SEQ ID NO:2, as well as fragments, biologically active portions, and variants thereof.

"Fragments" or "biologically active portions" include polypeptide fragments suitable for use as immunogens to raise anti-kinase antibodies. Fragments include peptides comprising amino acid sequences sufficiently identical to or derived from the amino acid sequences of a kinase protein of the invention and exhibiting at least one activity of a kinase protein, but which include fewer amino acids than the full-length kinase proteins disclosed herein. Typically, biologically active portions comprise a domain or motif with at least one. activity of the kinase protein. A biologically active portion of a kinase protein can be a polypeptide which is, for example, 20, 25, 50, 100 or more amino acids in length. Such biologically active portions can be prepared by recombinant techniques and evaluated for one or more of the functional activities of a native kinase protein.

By "variants" is intended proteins or polypeptides having an amino acid sequence that is at least about 70%, preferably about 75%, 80%, 85%, 90%, 91%, 92%, 93%, 94%, 95%, 96%, 97%, 98%, or 99% identical to the amino acid sequence of SEQ ID NO:2. Variants also include polypeptides encoded by the cDNA insert of the plasmid deposited with ATCC as Accession Number PTA-2333, or polypeptides encoded by a nucleic acid molecule that hybridizes to a nucleic acid molecule of SEQ ID NO:1 or a complement thereof under stringent conditions. Such variants generally will retain the functional activity of the kinase proteins of the invention. Variants include polypeptides that differ in amino acid sequence due to natural allelic variation or mutagenesis.

The invention also provides kinase chimeric or fusion proteins. As used herein, a kinase "chimeric protein" or "fusion protein" comprises a kinase polypeptide operably linked to a non-kinase polypeptide. A "kinase polypeptide" refers to a polypeptide having an amino acid sequence corresponding to a kinase protein, whereas a "non-kinase polypeptide" refers to a polypeptide having an amino acid sequence corresponding to a protein that is not substantially identical to the kinase protein, e.g., a protein that is different from the kinase protein and which is derived from the same or a different organism. Within a kinase fusion protein, the kinase polypeptide can correspond to all or a portion of a kinase protein, preferably at least one biologically active portion of a kinase protein. Within the fusion protein, the term "operably linked" is intended to indicate that the kinase polypeptide and the non-kinase polypeptide are fused in-frame to each other. The non-kinase polypeptide can be fused to the N-terminus or C-terminus of the kinase polypeptide.

One useful fusion protein is a GST-kinase fusion protein in which the kinase sequences are fused to the C-terminus of the GST sequences. Such fusion proteins can facilitate the purification of recombinant kinase proteins.

In yet another embodiment, the fusion protein is a kinase-immunoglobulin fusion protein in which all or part of a kinase protein is fused to sequences derived from a member of the immunoglobulin protein family. The kinase-immunoglobulin fusion proteins of the invention can be incorporated into pharmaceutical compositions and administered to a subject to inhibit an interaction between a kinase ligand and a kinase protein on the surface of a cell, thereby suppressing kinase-mediated signal transduction in vivo. The kinase-immunoglobulin fusion proteins can be used to affect the bioavailability of a kinase cognate ligand. Inhibition of the kinase ligand/kinase interaction may be useful therapeutically, both for treating proliferative and differentiative disorders and for modulating (e.g., promoting or inhibiting) cell survival. Moreover, the kinase-immunoglobulin fusion proteins of the invention can be used as immunogens to produce anti-kinase antibodies in a subject, to purify kinase ligands, and in screening assays to identify molecules that inhibit the interaction of a kinase protein with a kinase ligand.

Preferably, a kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a kinase-encoding nucleic acid can be cloned into a commercially available expression vector such that it is linked in-frame to an existing fusion moiety. Variants of the kinase protein can function as either kinase agonists (mimetics) or as kinase antagonists. Variants of the kinase protein can be generated by mutagenesis, e.g., discrete point mutation or truncation of the kinase protein. An agonist of the kinase protein can retain substantially the same or a subset of the biological activities of the naturally occurring form of the kinase protein. An antagonist of the kinase protein can inhibit one or more of the activities of the naturally occurring form of the kinase protein by, for example, competitively binding to a downstream or upstream member of a cellular signaling cascade that includes the kinase protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the kinase proteins.

Variants of the kinase protein that function as either kinase agonists or as kinase antagonists can be identified by screening combinatorial libraries of mutants, e.g., truncation mutants, of the kinase protein for kinase protein agonist or antagonist activity. In one embodiment, a variegated library of kinase variants is generated by combinatorial mutagenesis at the nucleic acid level and is encoded by a variegated gene library. A variegated library of kinase variants can be produced by, for example, enzymatically ligating a mixture of synthetic oligonucleotides into gene sequences such that a degenerate set of potential kinase sequences is expressible as individual polypeptides, or alternatively, as a set of larger fusion proteins (e.g., for phage display) containing the set of kinase sequences therein. There are a variety of methods that can be used to produce libraries of potential kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase sequences. Methods for synthesizing degenerate oligonucleotides are known in the art (see, e.g., Narang (1983) *Tetrahedron* 39:3; Itakura et al. (1984) *Annu. Rev. Biochem*. 53:323; Itakura et al. (1984) *Science* 198:1056; Ike et al. (1983) *Nucleic Acid Res*. 11:477).

In addition, libraries of fragments of the kinase protein coding sequence can be used to generate a variegated population of kinase fragments for screening and subsequent selection of variants of a kinase protein. In one embodiment, a library of coding sequence fragments can be generated by treating a double-stranded PCR fragment of a kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of kinase proteins. The most widely used techniques, which are amenable to high through-put analysis for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify kinase variants (Arkin and Yourvan (1992) *Proc. Natl. Acad. Sci. USA* 89:7811–7815; Delgrave et al. (1993) *Protein Engineering* 6(3):327–331).

An isolated kinase polypeptide of the invention can be used as an immunogen to generate antibodies that bind kinase proteins using standard techniques for polyclonal and monoclonal antibody preparation. The full-length kinase protein can be used or, alternatively, the invention provides antigenic peptide fragments of kinase proteins for use as immunogens. The antigenic peptide of a kinase protein comprises at least 8, preferably 10, 15, 20, or 30 amino acid residues of the amino acid sequence shown in SEQ ID NO:2 and encompasses an epitope of a kinase protein such that an antibody raised against the peptide forms a specific immune complex with the kinase protein. Preferred epitopes encompassed by the antigenic peptide are regions of a kinase protein that are located on the surface of the protein, e.g., hydrophilic regions. Analysis of the coding region from the 14189 polypeptide predicts hydrophilic regions from about amino acid 10 to about amino acid 22, from about amino acid 30 to about amino acid 40, from about amino acid 50 to about amino acid 60, from about amino acid 68 to about amino acid 72, from about amino acid 80 to about amino acid 90, from about amino acid 132 to about amino acid 142, from about amino acid 168 to about amino acid 177, from about amino acid 180 to about amino acid 188, from about amino acid 213 to about amino acid 250, from about amino acid 258 to about amino acid 265, from about amino acid 290 to about amino acid 330, from about amino acid 335 to about amino acid 340, from about amino acid 350 to about amino acid 420, from about amino acid 428 to about amino acid 440, from about amino acid 472 to about amino acid 480, and from about amino acid 485 to about amino acid 508.

Accordingly, another aspect of the invention pertains to anti-kinase polyclonal and monoclonal antibodies that bind a kinase protein. Polyclonal anti-kinase antibodies can be prepared by immunizing a suitable subject (e.g., rabbit, goat, mouse, or other mammal) with a kinase immunogen. The anti-kinase antibody titer in the immunized subject can be monitored over time by standard techniques, such as with an enzyme linked immunosorbent assay (ELISA) using immobilized kinase protein. At an appropriate time after immunization, e.g., when the anti-kinase antibody titers are highest, antibody-producing cells can be obtained from the subject and used to prepare monoclonal antibodies by standard techniques, such as the hybridoma technique originally described by Kohler and Milstein (1975) *Nature* 256:495–497,the human B-cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-kinase antibody can be identified and isolated by screening a recombinant combinatorial immunoglobulin library (e.g., an antibody phage display library) with a kinase protein to thereby isolate immunoglobulin library members that bind the kinase protein. Kits for generating and screening phage display libraries are commercially available (e.g., the Pharmacia *Recombinant Phage Antibody System*, Catalog No. 27-9400-01; and the Stratagene *SurfZAP™Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671;European Patent Application Nos. 184,187, 171, 496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl Cancer Inst.* 80:1553–1559); Morrison (1985) *Science* 229:1202–1207;Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-kinase antibody (e.g., monoclonal antibody) can be used to isolate kinase proteins by standard techniques, such as affinity chromatography or immunoprecipitation. An anti-kinase antibody can facilitate the purification of natural kinase protein from cells and of recombinantly produced kinase protein expressed in host cells. Moreover, an anti-kinase antibody can be used to detect kinase protein (e.g., in a cellular lysate or cell supernatant) in order to evaluate the abundance and pattern of expression of the kinase protein. Anti-kinase antibodies can be used diagnostically to monitor protein levels in tissue as part of a clinical testing procedure to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a kinase protein of the invention (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication-defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequen ce in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., kinase proteins, mutant forms of kinase proteins, fusion proteins, etc.).

The recombinant expression vectors of the invention can be designed for expression of kinase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, Calif.), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cerevisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or SV40 transformed simian kidney cells (COS). In mammalian cells, the expression vector's control functions are often provided by viral regulatory elements. For example, commonly used promoters are derived from polyoma, Adenovirus 2,cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), particular promoters of T-cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine homeobox (hox) promoter (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews-Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) kinase protein. Accordingly, the invention further provides methods for producing kinase protein using the host cells of the invention. In one embodiment, the method comprises culturing the host cell of the invention, into which a recombinant expression vector encoding a kinase protein has been introduced, in a suitable medium such that kinase protein is produced. In another embodiment, the method further comprises isolating kinase protein from the medium or the host cell.

The host cells of the invention can also be used to produce nonhuman transgenic animals. For example, in one embodiment, a host cell of the invention is a fertilized oocyte or an embryonic stem cell into which kinase-coding sequences have been introduced. Such host cells can then be used to create nonhuman transgenic animals in which exogenous kinase sequences have been introduced into their genome or homologous recombinant animals in which endogenous kinase sequences have been altered. Such animals are useful for studying the function and/or activity of kinase genes and proteins and for identifying and/or evaluating modulators of kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing kinase-encoding nucleic acid into the male pronuclei of a fertilized oocyte, e.g., by microinjection, retroviral infection, and allowing the oocyte to develop in a pseudopregnant female foster animal. The kinase cDNA sequence can be introduced as a transgene into the genome of a nonhuman animal. Alternatively, a homologue of the mouse kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the kinase transgene to direct expression of kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the kinase transgene in its genome and/or expression of kinase mRNA in tissues or cells of the animals. A transgenic founder animal can then be used to breed additional animals carrying the transgene. Moreover, transgenic animals carrying a transgene encoding kinase gene can further be bred to other transgenic animals carrying other transgenes.

To create a homologous recombinant animal, one prepares a vector containing at least a portion of a kinase gene or a homologue of the gene into which a deletion, addition, or substitution has been introduced to thereby alter, e.g., functionally disrupt, the kinase gene. In a preferred embodiment, the vector is designed such that, upon homologous recombination, the endogenous kinase gene is functionally disrupted (i.e., no longer encodes a functional protein; such vectors are also referred to as "knock out" vectors). Alternatively, the vector can be designed such that, upon homologous recombination, the endogenous kinase gene is mutated or otherwise altered but still encodes functional protein (e.g., the upstream regulatory region can be altered to thereby alter the expression of the endogenous kinase protein). In the homologous recombination vector, the altered portion of the kinase gene is flanked at its 5' and 3' ends by additional nucleic acid of the kinase gene to allow for homologous recombination to occur between the exogenous kinase gene carried by the vector and an endogenous kinase gene in an embryonic stem cell. The additional flanking kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced kinase gene has homologously recombined with the endogenous kinase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two trans genic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The kinase nucleic acid molecules, kinase proteins, and modulators thereof (e.g., anti-kinase antibodies) (also referred to herein as "active compounds") of the invention can be incorporated into pharmaceutical compositions suitable for administration. Such compositions typically comprise the nucleic acid molecule, protein, or modulators (e.g., antibody or small molecules and a pharmaceutically acceptable carrier). As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about I microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a kinase protein or anti-kinase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 $\mu$g/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecule of the invention can be used to express kinase protein (e.g., via a recombinant expression vector in a host cell in gene therapy applications), to detect kinase mRNA (e.g., in a biological sample) or a genetic lesion in a kinase gene, and to modulate kinase activity. In addition, the kinase protein can be used to screen drugs or compounds that modulate cellular growth and/or metabolism as well as to treat disorders characterized by insufficient or excessive production of kinase protein or production of kinase protein forms that have decreased or aberrant activity compared to kinase wild type protein. In addition, the anti-kinase antibodies of the invention can be used to detect and isolate kinase proteins and modulate kinase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to the kinase proteins of the invention or have a stimulatory or inhibitory effect on, for example, kinase expression or kinase activity.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422;Zuckermann et al. (1994).J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061;and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869), orphage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

Determining the ability of the test compound to bind to the kinase protein can be accomplished, for example, by coupling the test compound with a radioisotope or enzymatic label such that binding of the test compound to the kinase protein or biologically active portion thereof can be determined by detecting the labeled compound in a complex. For example, test compounds can be labeled with $^{125}$I, $^{35}$S, $^{14}$C, or $^3$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the kinase protein to bind to or interact with a kinase target molecule. By "target molecule" is intended a molecule with which a kinase protein binds or interacts in nature. In a preferred embodiment, the ability of the kinase protein to bind to or interact with a kinase target molecule can be determined by monitoring the activity of the target molecule. For example, the activity of the target molecule can be monitored by detecting induction of a cellular second messenger of the target (e.g., intracellular $Ca^{2+}$, diacylglycerol, IP3,etc.), detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), or detecting a cellular response, for example, cellular growth, differentiation, or proliferation.

In yet another embodiment, an assay of the present invention is a cell-free assay comprising contacting a kinase protein or biologically active portion thereof with a test compound and determining the ability of the test compound to bind to the kinase protein or biologically active portion thereof. Binding of the test compound to the kinase protein can be determined either directly or indirectly as described above. In a preferred embodiment, the assay includes contacting the kinase protein or biologically active portion thereof with a known compound that binds kinase protein to form an assay mixture, contacting the assay mixture with a test compound, and determining the ability of the test compound to preferentially bind to kinase protein or biologically active portion thereof as compared to the known compound.

In another embodiment, an assay is a cell-free assay comprising contacting kinase protein or biologically active portion thereof with a test compound and determining the ability of the test compound to modulate (e.g., stimulate or inhibit) the activity of the kinase protein or biologically active portion thereof. Determining the ability of the test compound to modulate the activity of a kinase protein can be accomplished, for example, by determining the ability of the kinase protein to bind to a kinase target molecule as described above for determining direct binding. In an alternative embodiment, determining the ability of the test compound to modulate the activity of a kinase protein can be accomplished by determining the ability of the kinase protein to further modulate a kinase target molecule. For example, the catalytic/enzymatic activity of the target molecule on an appropriate substrate can be determined as previously described.

In yet another embodiment, the cell-free assay comprises contacting the kinase protein or biologically active portion thereof with a known compound that binds a kinase protein to form an assay mixture, contacting the assay mixture with a test compound, and determining the ability of the test compound to preferentially bind to or modulate the activity of a kinase target molecule.

In the above-mentioned assays, it may be desirable to immobilize either a kinase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/kinase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of kinase binding or activity determined using standard techniques.

Other techniques for immobilizing proteins on matrices can also be used in the screening assays of the invention. For example, either kinase protein or its target molecule can be immobilized utilizing conjugation of biotin and streptavidin. Biotinylated kinase molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a kinase protein or target molecules but which do not interfere with binding of the kinase protein to its target molecule can be derivatized to the wells of the plate, and unbound target or kinase protein trapped in the wells by antibody conjugation. Methods for detecting such complexes, in addition to those described above for the GST-immobilized complexes, include immunodetection of complexes using antibodies reactive with the kinase protein or target molecule,as well as enzyme-linked assays that rely on detecting an enzymatic activity associated with the kinase protein or target molecule.

In another embodiment, modulators of kinase expression are identified in a method in which a cell is contacted with a candidate compound and the expression of kinase mRNA or protein in the cell is determined relative to expression of kinase mRNA or protein in a cell in the absence of the candidate compound. When expression is greater (statistically significantly greater) in the presence of the candidate compound than in its absence, the candidate compound is identified as a stimulator of kinase mRNA or protein expression. Alternatively, when expression is less (statistically significantly less) in the presence of the candidate compound than in its absence, the candidate compound is identified as an inhibitor of kinase mRNA or protein expression. The level of kinase mRNA or protein expression in the cells can be determined by methods described herein for detecting kinase mRNA or protein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with kinase protein ("kinase-binding proteins" or "kinase-bp") and modulate kinase activity. Such kinase-binding proteins are also likely to be involved in the propagation of signals by the kinase proteins as, for example, upstream or downstream elements of a signaling pathway.

This invention further pertains to novel agents identified by the above-described screening assays and uses thereof for treatments as described herein.

B. Detection Assays

Portions or fragments of the cDNA sequence identified herein (and the corresponding complete gene sequence) can be used in numerous ways as polynucleotide reagents. For example, the sequence can be used to: (1) map the respective gene on a chromosome; (2) identify an individual from a minute biological sample (tissue typing); and (3) aid in forensic identification of a biological sample. These applications are described in the subsections below.

1. Chromosome Mapping

The isolated kinase cDNA sequence of the invention can be used to map the respective kinase gene on a chromosome, thereby facilitating the location of gene regions associated with genetic disease. Computer analysis of the kinase sequence can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the kinase sequence of the invention will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map a kinase sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of kinase genes uses kinase polypeptides and fragments and sequences of the present invention and antibodies specific thereto. This mapping can be carried out by specifically detecting the presence of a kinase polypeptide in members of a panel of somatic cell hybrids between cells of a first species of animal from which the protein originates and cells from a second species of animal, and then determining which somatic cell hybrid(s) expresses the polypeptide and noting the chromosomes(s) from the first species of animal that it contains. For examples of this technique, see Pajunen et al. (1988) *Cytogenet. Cell. Genet.* 47:37–41 and Van Keuren et al. (1986) *Hum. Genet.* 74:34–40. Alternatively, the presence of a kinase polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The nucleotide sequence of the present invention is useful as an additional DNA marker for RFLP (described in U.S. Pat. No. 5,272,057).

Furthermore, the sequences of the present invention can be used to provide an alternative technique for determining the actual base-by-base DNA sequence of selected portions of an individual's genome. Thus, the kinase sequence of the invention can be used to prepare two PCR primers from the 5' and 3' ends of the sequence. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. The sequence described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If predicted coding sequences, such as those in SEQ ID NO:1 are used, a more appropriate number of primers for positive individual identification would be 500 to 2,000.

3. Use of Partial Kinase Sequences in Forensic Biology

DNA-based identification techniques can also be used in forensic biology. In this manner, PCR technology can be used to amplify DNA sequences taken from very small biological samples such as tissues, e.g., hair, skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions making it easier to differentiate individuals using this technique. An example of such useful polynucleotide reagents includes the kinase sequence or portions or fragments thereof, derived from the noncoding regions of SEQ ID NO:1 having a length of at least 20 or 30 bases.

The kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such kinase probes, can be used to identify tissue by species and/or by organ type.

In a similar fashion, these reagents, e.g., kinase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting kinase protein and/or nucleic acid expression as well as kinase activity, in the context of a biological sample. An exemplary method for detecting the presence or absence of kinase protein of the invention in a biological sample involves obtaining a biological sample from a test subject and contacting the biological sample with a compound or an agent capable of detecting kinase protein or nucleic acid (e.g., mRNA, genomic DNA) that encodes kinase protein of the invention such that the presence of kinase protein is detected in the biological sample. Results obtained with a biological sample from the test subject may be compared to results obtained with a biological sample from a control subject.

One agent for detecting kinase mRNA or genomic DNA is a labeled nucleic acid probe capable of hybridizing to kinase mRNA or genomic DNA of the invention. The nucleic acid probe can be, for example, a full-length or partial kinase nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to kinase mRNA or genomic DNA of the invention. Other suitable probes for use in the diagnostic assays of the invention are described herein.

A preferred agent for detecting kinase protein is an antibody capable of binding to kinase protein of the invention, preferably an antibody with a detectable label. Antibodies can be polyclonal, or more preferably, monoclonal. An intact antibody, or a fragment thereof (e.g., Fab or F(ab)'$_2$ )can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect kinase mRNA, protein, or genomic DNA in a biological sample in vitro as well as in vivo. For example, in vitro techniques for detection of kinase mRNA include Northern hybridizations and in situ hybridizations. In vitro techniques for detection of kinase protein include enzyme linked immunosorbent assays (ELISAs), Western blots, immunoprecipitations, and immunofluorescence. In vitro techniques for detection of kinase genomic DNA include Southern hybridizations. Furthermore, in vivo techniques for detection of kinase protein include introducing into a subject a labeled anti-kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Biological samples may be obtained from blood, serum, cells, or tissue of a subject.

The invention also encompasses kits for detecting the presence of kinase proteins in a biological sample (a test sample). Such kits can be used to determine if a subject is suffering from or is at increased risk of developing a disorder associated with aberrant expression of kinase protein. For example, the kit can comprise a labeled compound or agent capable of detecting kinase protein or mRNA in a biological sample and means for determining the amount of a kinase protein in the sample (e.g., an anti-kinase antibody such as an anti-h14189 kinase antibody or an oligonucleotide probe that binds to DNA encoding a kinase protein of the invention such as SEQ ID NO:1). Kits can also include instructions for observing that the tested subject is suffering from or is at risk of developing a disorder associated with aberrant expression of kinase sequences of the invention if the amount of kinase protein or mRNA is above or below a normal level.

For antibody-based kits, the kit can comprise, for example: (1) a first antibody (e.g., attached to a solid support) that binds to the kinase protein of the invention; and, optionally, (2) a second, different antibody that binds to kinase protein of the invention or the first antibody and is conjugated to a detectable agent. For oligonucleotide-based kits, the kit can comprise, for example: (1) an oligonucleotide, e.g., a detectably labeled oligonucleotide, that hybridizes to a kinase nucleic acid sequence of the invention or (2) a pair of primers useful for amplifying a kinase nucleic acid molecule of the invention.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of kinase proteins of the invention.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a kinase nucleic acid, preferably purified, polypeptide, preferably purified, or antibody, and thereby evaluating the plurality of capture probes. Binding, e.g., in the case of a nucleic acid, hybridization, with a capture probe at an address of the plurality, is detected, e.g., by signal generated from a label attached to the kinase nucleic acid, polypeptide, or antibody. The capture probes can be a set of nucleic acids from a selected sample, e.g., a sample of nucleic acids derived from a control or non-stimulated tissue or cell.

The method can include contacting the kinase nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a kinase sequence of the invention. Such methods can be used to diagnose a subject, e.g., to evaluate risk for a disease or disorder, to evaluate suitability of a selected treatment for a subject, to evaluate whether a subject has a disease or disorder.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a kinase polypeptide of the invention or from a cell or subject in which a kinase-mediated response has been elicited, e.g., by contact of the cell with a kinase nucleic acid or protein of the invention, or administration to the cell or subject a kinase nucleic acid or protein of the invention; contacting the array with one or more inquiry probes, wherein an inquiry probe can be a nucleic acid, polypeptide, or antibody (which is preferably other than a kinase nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a kinase sequence of the invention (or does not express as highly as in the case of the kinase positive plurality of capture probes) or from a cell or subject in which a kinase-mediated response has not been elicited (or has been elicited to a lesser extent than in the first sample); contacting the array with one or more inquiry probes (which is preferably other than a kinase nucleic acid, polypeptide, or antibody of the invention), and thereby evaluating the plurality of capture probes. Binding (e.g., in the case of a nucleic acid, hybridization) with a capture probe at an address of the plurality, is detected, e.g., by a signal generated from a label attached to the nucleic acid, polypeptide, or antibody.

In another aspect, the invention features a method of analyzing a kinase sequence of the invention, e.g., analyzing structure, function, or relatedness to other nucleic acid or amino acid sequences. The method includes: providing a kinase nucleic acid or amino acid sequence, e.g., the 14189 sequence set forth in SEQ ID NO:1 or SEQ ID NO:2 or a portion thereof; comparing the kinase sequence with one or more preferably a plurality of sequences from a collection of sequences, e.g., a nucleic acid or protein sequence database; to thereby analyze the kinase sequence of the invention.

The method can include evaluating the sequence identity between a kinase sequence of the invention, e.g., the 14189 sequence, and a database sequence. The method can be performed by accessing the database at a second site, e.g., over the internet.

In another aspect, the invention features, a set of oligonucleotides, useful, e.g., for identifying SNP's, or identifying specific alleles of a kinase sequence of the invention, e.g., the 14189 sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with kinase protein, kinase nucleic acid expression, or kinase activity of the invention. Prognostic assays can be used for prognostic or predictive purposes to thereby prophylactically treat an individual prior to the onset of a disorder characterized by or associated with kinase protein, kinase nucleic acid expression, or kinase activity of the invention.

Thus, the present invention provides a method in which a test sample is obtained from a subject, and kinase protein or nucleic acid of the invention (e.g., mRNA, genomic DNA) is detected, wherein the presence of kinase protein or nucleic acid is diagnostic for a subject having or at risk of developing a disease or disorder associated with aberrant kinase expression or activity. As used herein, a "test sample" refers to a biological sample obtained from a subject of interest. For example, a test sample can be a biological fluid cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease kinase activity) to effectively treat a disease or disorder associated with aberrant kinase expression or activity. In this manner, a test sample is obtained and kinase protein or nucleic acid is detected. The presence of kinase protein or nucleic acid of the invention is diagnostic for a subject that can be administered the agent to treat a disorder associated with aberrant kinase expression or activity.

The methods of the invention can also be used to detect genetic lesions or mutations in a kinase gene of the invention, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a kinase-protein, or the misexpression of the kinase gene of the invention. For example, such genetic lesions or mutations can be detected by ascertaining the existence of at least one of: (1) a deletion of one or more nucleotides from a kinase gene; (2) an addition of one or more nucleotides to a kinase gene; (3) a substitution of one or more nucleotides of a kinase gene; (4) a chromosomal rearrangement of a kinase gene; (5) an alteration in the level of a messenger RNA transcript of a kinase gene; (6) an aberrant modification of a kinase gene, such as of the methylation pattern of the genomic DNA; (7) the presence of a non-wild-type splicing pattern of a messenger RNA transcript of a kinase gene; (8) a non-wild-type level of a kinase-protein; (9) an allelic loss of a kinase gene; and (10) an inappropriate post-translational modification of a kinase-protein. As described herein, there are a large number of assay techniques known in the art that can be used for detecting lesions in a kinase gene. Any cell type or tissue in which kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080;and Nakazawa et al. (1994) Proc. Natl. Acad. Sci. USA 91:360–364), the latter of which can be particularly useful for detecting point mutations in the kinase-gene (see, e.g., Abravaya et al. (1995) Nucleic Acids Res. 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) Proc. Natl. Acad. Sci. USA 87:1874–1878), transcriptional amplification system (Kwoh et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a kinase molecule can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). In yet another embodiment, any of a variety of sequencing reactions known in the art can be used to directly sequence the kinase gene and detect mutations by comparing the sequence of the sample kinase gene with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162;and Griffin et al. (1993) Appl. Biochem. Biotechnol. 38:147–159).

Other methods for detecting mutations in the kinase gene include methods in which protection from cleavage agents is used to detect mismatched bases in RNA/RNA or RNA/DNA heteroduplexes (Myers et al. (1985) Science 230:1242). See, also Cotton et al. (1988) Proc. Natl. Acad. Sci. USA 85:4397;Saleeba et al. (1992) Methods Enzymol. 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in kinase cDNAs obtained from samples of cells. See, e.g., Hsu et al. (1994) Carcinogenesis 15:1657–1662. According to an exemplary embodiment, a probe based on a kinase sequence, e.g., a wild-type kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766;see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In another embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a kinase gene.

4. Pharmacogenomics

Agents or modulators that have a stimulatory or inhibitory effect on kinase activity (e.g., kinase gene expression) as identified by a screening assay described herein, can be administered to individuals to treat (prophylactically or therapeutically) disorders associated with aberrant kinase activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of kinase protein, expression of kinase nucleic acid, or mutation content of kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266.In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a kinase protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a kinase molecule or kinase modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a kinase molecule or kinase modulator of the invention, such as a modulator identified by one of the exemplary screening assays described herein.

The present invention further provides methods for identifying new agents, or combinations, that are based on identifying agents that modulate the activity of one or more of the gene products encoded by one or more of the kinase genes of the present invention, wherein these products may be associated with resistance of the cells to a therapeutic agent. Specifically, the activity of the proteins encoded by the kinase genes of the present invention can be used as a basis for identifying agents for overcoming agent resistance. By blocking the activity of one or more of the resistance proteins, target cells, will become sensitive to treatment with an agent that the unmodified target cells were resistant to.

Monitoring the influence of agents (e.g., drugs) on the expression or activity of a kinase protein can be applied in clinical trials. For example, the effectiveness of an agent determined by a screening assay as described herein to increase kinase gene expression, protein levels, or up-regulate kinase activity, can be monitored in clinical trials of subjects exhibiting decreased kinase gene expression, protein levels, or down-regulated kinase activity. Alternatively, the effectiveness of an agent determined by a screening assay to decrease kinase gene expression, protein levels, or down-regulate kinase activity, can be monitored in clinical trials of subjects exhibiting increased kinase gene expression, protein levels, or up-regulated kinase activity. In such clinical trials, the expression or activity of a kinase gene, and preferably, other genes that have been implicated in, for example, a kinase-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of kinase protein, expression of kinase nucleic acid, or mutation content of kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a kinase modulator, such as a modulator identified by one of the screening assays described herein.

5. Monitoring of Effects During Clinical Trials

Monitoring the influence of agents (e.g., drugs, compounds) on the expression or activity of kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease kinase gene expression, protein levels, or protein activity, can be monitored in clinical trials of subjects exhibiting decreased or increased kinase gene expression, protein levels, or protein activity. In such clinical trials, kinase expression or activity and preferably that of other genes that have been implicated in for example, a cellular proliferation disorder, can be used as a marker of cellular growth and differentiation.

For example, and not by way of limitation, genes that are modulated in cells by treatment with an agent (e.g., compound, drug, or small molecule) that modulates kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a kinase protein, mRNA, or genomic DNA in the preadministration sample; (3) obtaining one or more post-administration samples from the subject; (4) detecting the level of expression or activity of the kinase protein, mRNA, or genomic DNA in the postadministration samples; (5) comparing the level of expression or activity of the kinase protein, mRNA, or genomic DNA in the preadministration sample with the kinase protein, mRNA, or genomic DNA in the postadministration sample or samples; and (vi) altering the administration of the agent to the subject accordingly to bring about the desired effect, i.e., for example, an increase or a decrease in the expression or activity of a kinase protein.

C. Methods of Treatment

The present invention provides for both prophylactic and therapeutic methods of treating a subject at risk of (or susceptible to) a disorder or having a disorder associated with aberrant kinase expression or activity. Additionally, the compositions of the invention find use in the treatment of disorders described herein.

1. Prophylactic Methods

In one aspect, the invention provides a method for preventing in a subject a disease or condition associated with an aberrant kinase expression or activity by administering to the subject an agent that modulates kinase expression or at least one kinase gene activity. Subjects at risk for a disease that is caused, or contributed to, by aberrant kinase expression or activity can be identified by, for example, any or a combination of diagnostic or prognostic assays as described herein. Administration of a prophylactic agent can occur prior to the manifestation of symptoms characteristic of the kinase aberrancy, such that a disease or disorder is prevented or, alternatively, delayed in its progression. Depending on the type of kinase aberrancy, for example, a kinase agonist or kinase antagonist agent can be used for treating the subject. The appropriate agent can be determined based on screening assays described herein.

2. Therapeutic Methods

Another aspect of the invention pertains to methods of modulating kinase expression or activity for therapeutic purposes. The modulatory method of the invention involves contacting a cell with an agent that modulates one or more of the activities of kinase protein activity associated with the cell. An agent that modulates kinase protein activity can be an agent as described herein, such as a nucleic acid or a protein, a naturally occurring cognate ligand of a kinase protein, a peptide, a kinase peptidomimetic, or other small molecule. In one embodiment, the agent stimulates one or more of the biological activities of kinase protein. Examples of such stimulatory agents include active kinase protein and a nucleic acid molecule encoding a kinase protein that has been introduced into the cell. In another embodiment, the agent inhibits one or more of the biological activities of kinase protein. Examples of such inhibitory agents include antisense kinase nucleic acid molecules and anti-kinase antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a kinase protein or nucleic acid molecule. In one embodiment, the method involves administering an agent (e.g., an agent identified by a screening assay described herein), or a combination of agents, that modulates (e.g., up-regulates or down-regulates) kinase expression or activity. In another embodiment, the method involves administering a kinase protein or nucleic acid molecule as therapy to compensate for reduced or aberrant kinase expression or activity.

Stimulation of kinase activity is desirable in situations in which a kinase protein is abnormally down-regulated and/or in which increased kinase activity is likely to have a beneficial effect. Conversely, inhibition of kinase activity is desirable in situations in which kinase activity is abnormally up-regulated and/or in which decreased kinase activity is likely to have a beneficial effect.

This invention is further illustrated by the following examples, which should not be construed as limiting.

EXPERIMENTAL

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using $\beta$-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Novel kinase expression was measured by TaqMan® quantitative PCR (Perkin Elmer Applied Biosystems) in cDNA prepared from the following human tissues and cell lines as shown in FIGS. 4A and 4B: lung; kidney; heart; spleen; fetal liver, normal liver (NDR 200, PIT 260), and fibrotic liver (LF/NDR 191, LF/NDR 194, LF/NDR 079, NDR 141, NDR 190, NDR 192, NDR 225, NDR 249, NDR 250, NDR 251, PIT 324, PIT 345), lymph nodes, and tonsil; non-cultured hepatocytes; HepG2 cells; HepG2 cells cultured in the presence of TGF-beta; HepG2 cells transfected with HBV; Hep3 cells cultured in normal and low oxygen; normal granulocytes; dermal and lung fibroblasts cultured with and without TGF-beta; quiescent, resting, and passaged stellate cells; resting and phytohemaglutinin-activated peripheral blood mononuclear cells (PBMC); CD3$^+$; CD4$^+$; and CD8$^+$ T cells; T-cell line (Molt 4), Th1 and Th2 cells stimulated for 24 hours with anti-CD3 antibody and JY cells; resting and lipopolysaccharide activated CD19$^+$ B cells; CD14$^+$ cells; CD14$^-$/CD15$^+$ cells; CD34$^+$ cells from mobilized peripheral blood (MPB CD34$^+$); adult resting bone marrow (ABM CD34$^+$); mobilized adult bone marrow (MBM CD11b$^-$); bone marrow mononuclear cells (BM MNC); neonatal umbilical cord; erythroid cells; megakaryocytes; neutrophils; hepatitic-C virus-infected liver (HCV); transformed human cell lines included an erythroleukemia (K562); and an acute promyelocytic leukemia (HL60). A no template control (NTC) was used as the reference sample.

Probes were designed by PrimerExpress software (PE Biosystems) based on the sequence of the h14189 kinase gene. The primers and probes for expression analysis of h14189 and for $\beta$-2 microglobulin are as follows:

| | | |
|---|---|---|
| h14189 Forward Primer | ACCGCAGCCGCGTCT | (SEQ ID NO:5) |
| h14189 Reverse Primer | TCTCTCTCGAGGTGCCGCT | (SEQ ID NO:6) |
| h14189 TaqMan Probe | TCAGATGATCCTGGAGTGTGGAGGCA | (SEQ ID NO:7) |
| β-2 microglobulin Forward Primer | CACCCCCACTGAAAAAGATGA | (SEQ ID NO:8) |
| β-2 microglobulin Reverse Primer | CTTAACTATCTTGGGCTGTGACAAAG | (SEQ ID NO:9) |
| β-2 microglobulin TaqMan Prober | TATGCCTGCCGTGTGAACCACGTG | (SEQ ID NO:10) |

The h14189 kinase gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate h14189 kinase gene expression in the various tissues relative to β-2 microglobulin expression in the same tissue. The threshold cycle (Ct) value is defined as the cycle at which a statistically significant increase in flourescence is detected. A lower Ct value is indicative of a higher mRNA concentration. The Ct value of the kinase gene is normalized by subtracting the Ct value of the β-2 microglobulin gene to obtain a $_\Delta Ct$ value using the following formula: $_\Delta Ct = Ct_{kinase} - Ct_{\beta-2\ microglobulin}$. Expression is then calibrated against a cDNA sample showing a comparatively low level of expression of the kinase gene. The $_\Delta Ct$ value for the calibrator sample is then subtracted from $_\Delta Ct$ for each tissue sample according to the following formula: $_{\Delta\Delta}Ct = _\Delta Ct_{sample} - _\Delta Ct_{calibrator}$. Relative expression is then calculated using the arithmetic formula given by $2^{-\Delta\Delta Ct}$. Expression of the target kinase gene in each of the tissues tested is then graphically represented as discussed in more detail below.

FIGS. 4A and 4B show h14189 gene expression determined by TaqMan® quantitative PCR in various tissues and cell types. As shown in FIGS. 4A and 4B, the highest levels of h14189 expression were observed in normal kidney and lung tissue, HepG2 cells transfected with HBV (HepG2.2.15), fibrotic liver samples, a transformed human erythroleukemia cell line (K562), and cells from mobilized peripheral blood (MPB CD34+). Significant levels of h14189 expression were also observed in human hepatic stellate cells, spleen, tonsil, cord blood, bone marrow, and dermal fibroblasts.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising a nucleotide sequence that is at least 97% identical to the nucleotide sequence of SEQ ID NO: 1, at least 97% identical to nucleotides 48–1682 of SEQ ID NO: 1, or at least 97% identical to the cDNA insert of the plasmid deposited with ATCC as Accession Number PTA-2333, wherein the nucleic acid molecule encodes a polypeptide with kinase activity;
   b) a nucleic acid molecule comprising the nucleotide sequence of SEQ ID NO: 1, nucleotides 48–1682 of SEQ ID NO: 1, or the cDNA insert of the plasmid deposited with ATCC as Accession Number PTA-2333, wherein the nucleic acid molecule encodes a polypeptide with kinase activity;
   c) a nucleic acid molecule which encodes a polypeptide comprising the amino acid sequence of SEQ ID NO: 2, or the amino acid sequence encoded by the cDNA insert of the plasmid deposited with ATCC as Accession Number PTA-2333, wherein the nucleic acid molecule encodes a polypeptide with kinase activity; and
   d) a nucleic acid molecule which comprises the complement of the nucleic acid molecule of a), b) or c).

2. The nucleic acid molecule of claim 1 further comprising nucleic acid sequences encoding a heterologous polypeptide.

3. A kit comprising a nucleic acid molecule of claim 1 and instructions for use.

4. A host cell genetically engineered to contain the nucleic acid molecule of claim 1.

5. A host cell genetically engineered to contain the nucleic acid molecule of claim 2.

6. A host cell genetically engineered to express the nucleic acid molecule of claim 1.

7. A host cell genetically engineered to express the nucleic acid molecule of claim 2.

8. The host cell of claim 4 which is a mammalian host cell.

9. The host cell of claim 5 which is a mammalian host cell.

10. The host cell of claim 6 which is a mammalian host cell.

11. The host cell of claim 7 which is a mammalian host cell.

12. A vector comprising the nucleic acid molecule of claim 1.

13. A vector comprising the nucleic acid molecule of claim 2.

14. The vector of claim 12 further comprising a nucleic acid sequence which regulates expression of the nucleic acid molecule.

15. The vector of claim 13 further comprising a nucleic acid sequence which regulates expression of the nucleic acid molecule.

16. A host cell comprising the vector of claim 12.

17. A host cell comprising the vector of claim 13.

18. The host cell of claim 16 which is a mammalian host cell.

19. The host cell of claim 17 which is a mammalian host cell.

20. A method of producing a polypeptide comprising: culturing the host cell of claim 6 under conditions in which the nucleic acid molecule is expressed to produce said polypeptide.

21. A method of producing a polypeptide comprising: culturing the host cell of claim 7 under conditions in which the nucleic acid molecule is expressed to produce said polypeptide.

22. An isolated nucleic acid molecule selected from the group consisting of:

a) a nucleic acid molecule consisting of the nucleotide sequence of SEQ ID NO: 1, nucleotides 48–1682 of SEQ ID NO: 1, or the cDNA insert of the plasmid deposited with ATCC as Accession Number PTA-2333, wherein the nucleic acid molecule encodes a polypeptide with kinase activity; and b) a nucleic acid molecule which comprises the complement of the nucleic acid molecule of a).

* * * * *

SEQUENCE LISTING

<160> NUMBER OF SEQ ID NOS: 13

<210> SEQ ID NO 1
<211> LENGTH: 1914
<212> TYPE: DNA
<213> ORGANISM: Homo sapiens
<220> FEATURE:
<221> NAME/KEY: CDS
<222> LOCATION: (48)...(1682)
<221> NAME/KEY: misc_feature
<222> LOCATION: (1)...(1914)
<223> OTHER INFORMATION: n = A,T,C or G

<400> SEQUENCE: 1
gttccgaccm cgcgtccgcg gacgcgtggg cgggcgtcct ggccgcc atg tgc acc    56
                                                   Met Cys Thr
                                                    1

| | | |
|---|---|---|
| gta gtg gac cct cgc att gtc cgg aga tac cta ctc agg cgg cag ctc<br>Val Val Asp Pro Arg Ile Val Arg Arg Tyr Leu Leu Arg Arg Gln Leu<br>5                          10                   15 | | 104 |
| ggg cag ggg gcc tat ggc att gtg tgg aag gca gtg gac cgg agg act<br>Gly Gln Gly Ala Tyr Gly Ile Val Trp Lys Ala Val Asp Arg Arg Thr<br>20                       25                30                 35 | | 152 |
| ggt gag gtc gtg gcc atc aag aaa atc ttt gat gct ttt agg gat aag<br>Gly Glu Val Val Ala Ile Lys Lys Ile Phe Asp Ala Phe Arg Asp Lys<br>                  40                45                 50 | | 200 |
| aca gat gcc cag aga aca ttc cgg gaa atc acg ctc ctc cag gag ttt<br>Thr Asp Ala Gln Arg Thr Phe Arg Glu Ile Thr Leu Leu Gln Glu Phe<br>              55                    60                 65 | | 248 |
| ggg gac cat ccc aac atc atc agc ctc ctt gac gtg atc cgg gca gag<br>Gly Asp His Pro Asn Ile Ile Ser Leu Leu Asp Val Ile Arg Ala Glu<br>          70                    75                 80 | | 296 |
| aac gac agg gac att tac ctg gtg ttt gag ttt atg gac act gac ctg<br>Asn Asp Arg Asp Ile Tyr Leu Val Phe Glu Phe Met Asp Thr Asp Leu<br>        85                    90                95 | | 344 |
| aac gca gtc atc cgg aag ggc ggc ctg ctg cag gac gtc cac gtg cgc<br>Asn Ala Val Ile Arg Lys Gly Gly Leu Leu Gln Asp Val His Val Arg<br>100                 105               110              115 | | 392 |
| tcc atc ttc tac cag ctc ctg cgg gcc acc cgg ttc ctc cac tcg ggg<br>Ser Ile Phe Tyr Gln Leu Leu Arg Ala Thr Arg Phe Leu His Ser Gly<br>               120                  125              130 | | 440 |
| cac gtt gtg cac cgg gac cag aag ccg tcc aat gtg ctc ctg gat gcc<br>His Val Val His Arg Asp Gln Lys Pro Ser Asn Val Leu Leu Asp Ala<br>              135                 140              145 | | 488 |
| aac tgc aca gtg aag ctg tgt gac ttt ggc ctg gcc cgc tcc ctg ggc<br>Asn Cys Thr Val Lys Leu Cys Asp Phe Gly Leu Ala Arg Ser Leu Gly<br>         150                  155               160 | | 536 |
| gac ctc cct gag ggg cct gag gac cag gcc gtg aca gag tac gtg gcc<br>Asp Leu Pro Glu Gly Pro Glu Asp Gln Ala Val Thr Glu Tyr Val Ala<br>165                 170               175 | | 584 |
| aca cgc tgg tac cga gca ccg gag gtg ctg ctc tct tcg cac cga tac<br>Thr Arg Trp Tyr Arg Ala Pro Glu Val Leu Leu Ser Ser His Arg Tyr<br>180                 185               190              195 | | 632 |
| acc ctt ggg gtg gac atg tgg agt ctg ggc tgt atc ctg ggg gag atg<br>Thr Leu Gly Val Asp Met Trp Ser Leu Gly Cys Ile Leu Gly Glu Met<br>              200                 205              210 | | 680 |
| ctg cgg ggg aga ccc ctg ttc ccc ggc acg tcc acc ctn cac cag ctg<br>Leu Arg Gly Arg Pro Leu Phe Pro Gly Thr Ser Thr Xaa His Gln Leu<br>              215                 220              225 | | 728 |
| gag ctg atc ctg gag acc atc cca ccg cca tct gag gag gac ctc ctg<br>Glu Leu Ile Leu Glu Thr Ile Pro Pro Pro Ser Glu Glu Asp Leu Leu<br>         230                  235               240 | | 776 |
| gct ctc ggc tca ggc tgc cgt gcc tct gtg ctg cac cag ctg ggg tcc<br>Ala Leu Gly Ser Gly Cys Arg Ala Ser Val Leu His Gln Leu Gly Ser<br>245                 250               255 | | 824 |
| cgg cca cga cag acg ctg gat gcc ctc cta ccg cca gac acc tcc cca<br>Arg Pro Arg Gln Thr Leu Asp Ala Leu Leu Pro Pro Asp Thr Ser Pro<br>260                 265               270              275 | | 872 |
| gag gcc ttg gac ctc ctt agg cga ctc ctg gtg ttc gcc ccg gac aag<br>Glu Ala Leu Asp Leu Leu Arg Arg Leu Leu Val Phe Ala Pro Asp Lys<br>              280                 285              290 | | 920 |
| cgg tta agc gcg acc cag gca ctg cag cac ccc tac gtg cag agg ttc<br>Arg Leu Ser Ala Thr Gln Ala Leu Gln His Pro Tyr Val Gln Arg Phe<br>         295                  300               305 | | 968 |
| cac tgc ccc agc gac gag tgg gca cga gag gca gat gtg cgg ccc cgg<br>His Cys Pro Ser Asp Glu Trp Ala Arg Glu Ala Asp Val Arg Pro Arg | | 1016 |

```
                310                 315                 320
gca cac gaa ggg gtc cag ctc tct gtg cct gag tac cgc agc cgc gtc    1064
Ala His Glu Gly Val Gln Leu Ser Val Pro Glu Tyr Arg Ser Arg Val
    325                 330                 335 tat cag atg atc ctg gag tgt gga ggc agc agc ggc acc tcg aga gag    1112
Tyr Gln Met Ile Leu Glu Cys Gly Gly Ser Ser Gly Thr Ser Arg Glu
340                 345                 350                 355 aag ggc ccg gag ggt gtc tcc cca agc cag gca cac ctg cac aaa ccc    1160
Lys Gly Pro Glu Gly Val Ser Pro Ser Gln Ala His Leu His Lys Pro
                360                 365                 370 aga gcc gac cct cag ctg cct tct agg aca cct gtg cag ggt ccc aga    1208
Arg Ala Asp Pro Gln Leu Pro Ser Arg Thr Pro Val Gln Gly Pro Arg
            375                 380                 385 ccc agg ccc cag agc agc cca ggc cat gac cct gcc gag cac gag tcc    1256
Pro Arg Pro Gln Ser Ser Pro Gly His Asp Pro Ala Glu His Glu Ser
        390                 395                 400 ccc cgt gca gcc aag aac gtt ccc agg cag aac tcc gct ccc ctg ctc    1304
Pro Arg Ala Ala Lys Asn Val Pro Arg Gln Asn Ser Ala Pro Leu Leu
    405                 410                 415 caa act gct ctc cta ggg aat ggg gaa agg ccc cct ggg gcg aag gaa    1352
Gln Thr Ala Leu Leu Gly Asn Gly Glu Arg Pro Pro Gly Ala Lys Glu
420                 425                 430                 435 gcg ccc ccc ttg aca ctc tcg ctg gtg aag cca agc ggg agg gga gct    1400
Ala Pro Pro Leu Thr Leu Ser Leu Val Lys Pro Ser Gly Arg Gly Ala
                440                 445                 450 gcg ccc tcc ctg acc tcc cag gct gcg gct cag gtg gcc aac cag gcc    1448
Ala Pro Ser Leu Thr Ser Gln Ala Ala Ala Gln Val Ala Asn Gln Ala
            455                 460                 465 ctg atc cgg ggt gac tgg aac cgg ggc ggt ggg gtg agg gtg gcc agc    1496
Leu Ile Arg Gly Asp Trp Asn Arg Gly Gly Gly Val Arg Val Ala Ser
        470                 475                 480 gta caa cag gtc cct ccc cgg ctt cct ccg gag gcc cgg ccc ggc cgg    1544
Val Gln Gln Val Pro Pro Arg Leu Pro Pro Glu Ala Arg Pro Gly Arg
    485                 490                 495 agg atg ttc agc acc tct gcc ttg cag ggt gcc cag ggg ggt gcc agg    1592
Arg Met Phe Ser Thr Ser Ala Leu Gln Gly Ala Gln Gly Gly Ala Arg
500                 505                 510                 515 gct ttg ctt gga ggc tac tcc caa gcc tac ggg act gtc tgc cac tcg    1640
Ala Leu Leu Gly Gly Tyr Ser Gln Ala Tyr Gly Thr Val Cys His Ser
                520                 525                 530 gca ctg ggc cac ctg ccc ctg ctg gag ggg cac cat gtg tga            1682
Ala Leu Gly His Leu Pro Leu Leu Glu Gly His His Val *
            535                 540 gccgccctac tcccttcacc tggccctctg ttcctgcccc agcccttcc ccagacccct   1742 ctccagtctc ctgcacccct tagccctccc tgctttgcct ggcccgttga agttccaggg  1802
agcttgcccg ggtctcctcg ggggagcaga tgagggccct gccccgccc cactgacttt   1862 ctccaataaa gncatgtctg ccccccccc naaaaaaaaa aaaaaaaaa aa            1914
```

<210> SEQ ID NO 2
<211> LENGTH: 544
<212> TYPE: PRT
<213> ORGANISM: Homo sapiens
<220> FEATURE:
<221> NAME/KEY: VARIANT
<222> LOCATION: (1)...(544)
<223> OTHER INFORMATION: Xaa = Any Amino Acid

<400> SEQUENCE: 2

Met Cys Thr Val Val Asp Pro Arg Ile Val Arg Arg Tyr Leu Leu Arg

-continued

```
  1               5                   10                  15
Arg Gln Leu Gly Gln Gly Ala Tyr Gly Ile Val Trp Lys Ala Val Asp
             20                  25                  30

Arg Arg Thr Gly Glu Val Val Ala Ile Lys Lys Ile Phe Asp Ala Phe
             35                  40                  45

Arg Asp Lys Thr Asp Ala Gln Arg Thr Phe Arg Glu Ile Thr Leu Leu
 50                  55                  60

Gln Glu Phe Gly Asp His Pro Asn Ile Ile Ser Leu Leu Asp Val Ile
 65                  70                  75                  80

Arg Ala Glu Asn Asp Arg Asp Ile Tyr Leu Val Phe Glu Phe Met Asp
             85                  90                  95

Thr Asp Leu Asn Ala Val Ile Arg Lys Gly Gly Leu Leu Gln Asp Val
            100                 105                 110

His Val Arg Ser Ile Phe Tyr Gln Leu Leu Arg Ala Thr Arg Phe Leu
            115                 120                 125

His Ser Gly His Val Val His Arg Asp Gln Lys Pro Ser Asn Val Leu
            130                 135                 140

Leu Asp Ala Asn Cys Thr Val Lys Leu Cys Asp Phe Gly Leu Ala Arg
145                 150                 155                 160

Ser Leu Gly Asp Leu Pro Glu Gly Pro Glu Asp Gln Ala Val Thr Glu
            165                 170                 175

Tyr Val Ala Thr Arg Trp Tyr Arg Ala Pro Glu Val Leu Leu Ser Ser
            180                 185                 190

His Arg Tyr Thr Leu Gly Val Asp Met Trp Ser Leu Gly Cys Ile Leu
            195                 200                 205

Gly Glu Met Leu Arg Gly Arg Pro Leu Phe Pro Gly Thr Ser Thr Xaa
            210                 215                 220

His Gln Leu Glu Leu Ile Leu Glu Thr Ile Pro Pro Pro Ser Glu Glu
225                 230                 235                 240

Asp Leu Leu Ala Leu Gly Ser Gly Cys Arg Ala Ser Val Leu His Gln
            245                 250                 255

Leu Gly Ser Arg Pro Arg Gln Thr Leu Asp Ala Leu Leu Pro Pro Asp
            260                 265                 270

Thr Ser Pro Glu Ala Leu Asp Leu Leu Arg Arg Leu Leu Val Phe Ala
            275                 280                 285

Pro Asp Lys Arg Leu Ser Ala Thr Gln Ala Leu Gln His Pro Tyr Val
            290                 295                 300

Gln Arg Phe His Cys Pro Ser Asp Glu Trp Ala Arg Glu Ala Asp Val
305                 310                 315                 320

Arg Pro Arg Ala His Glu Gly Val Gln Leu Ser Val Pro Glu Tyr Arg
            325                 330                 335

Ser Arg Val Tyr Gln Met Ile Leu Glu Cys Gly Gly Ser Ser Gly Thr
            340                 345                 350

Ser Arg Glu Lys Gly Pro Glu Gly Val Ser Pro Ser Gln Ala His Leu
            355                 360                 365

His Lys Pro Arg Ala Asp Pro Gln Leu Pro Ser Arg Thr Pro Val Gln
            370                 375                 380

Gly Pro Arg Pro Arg Pro Gln Ser Ser Pro Gly His Asp Pro Ala Glu
385                 390                 395                 400

His Glu Ser Pro Arg Ala Ala Lys Asn Val Pro Arg Gln Asn Ser Ala
            405                 410                 415

Pro Leu Leu Gln Thr Ala Leu Leu Gly Asn Gly Glu Arg Pro Pro Gly
            420                 425                 430
```

-continued

```
Ala Lys Glu Ala Pro Pro Leu Thr Leu Ser Leu Val Lys Pro Ser Gly
        435                 440                 445

Arg Gly Ala Ala Pro Ser Leu Thr Ser Gln Ala Ala Gln Val Ala
        450                 455                 460

Asn Gln Ala Leu Ile Arg Gly Asp Trp Asn Arg Gly Gly Val Arg
465                 470                 475                 480

Val Ala Ser Val Gln Gln Val Pro Pro Arg Leu Pro Pro Glu Ala Arg
                485                 490                 495

Pro Gly Arg Arg Met Phe Ser Thr Ser Ala Leu Gln Gly Ala Gln Gly
                500                 505                 510

Gly Ala Arg Ala Leu Leu Gly Gly Tyr Ser Gln Ala Tyr Gly Thr Val
        515                 520                 525

Cys His Ser Ala Leu Gly His Leu Pro Leu Leu Glu Gly His His Val
        530                 535                 540
```

<210> SEQ ID NO 3
<211> LENGTH: 1998
<212> TYPE: DNA
<213> ORGANISM: Rattus norvegicus
<220> FEATURE:
<221> NAME/KEY: CDS
<222> LOCATION: (154)...(1794)

<400> SEQUENCE: 3

```
ctcagtagag agagagagag agagagacag acagacagac aagaaaagaa          60
aagaaaagga aaggaaagga aagaaaagaa aaaacaaagg ggcaggacta agaaaagaat  120
cggtggacaa agagccagcg tctgcctctc acc atg tgt gct gcc gag gtg gac  174
                                    Met Cys Ala Ala Glu Val Asp
                                      1               5 cgt cat gta tcc cag aga tac ctg atc aag cgg agg ctt ggg aag ggg  222
Arg His Val Ser Gln Arg Tyr Leu Ile Lys Arg Arg Leu Gly Lys Gly
         10                  15                  20 gcc tac ggc att gta tgg aag gcc atg gac cgg agg act ggt gag gta  270
Ala Tyr Gly Ile Val Trp Lys Ala Met Asp Arg Arg Thr Gly Glu Val
 25                  30                  35 gtg gcc atc aag aaa atc ttt gat gcc ttt agg gac cag aca gat gct  318
Val Ala Ile Lys Lys Ile Phe Asp Ala Phe Arg Asp Gln Thr Asp Ala
 40                  45                  50                  55 cag agg acc ttc cgt gaa atc atg ctt ctc cgg gag ttt ggg ggc cat  366
Gln Arg Thr Phe Arg Glu Ile Met Leu Leu Arg Glu Phe Gly Gly His
             60                  65                  70 ccc aac atc atc cgc ctg ctt gat gta atc cca gca aag aat gac agg  414
Pro Asn Ile Ile Arg Leu Leu Asp Val Ile Pro Ala Lys Asn Asp Arg
         75                  80                  85 gat att tac ctg gtg ttt gag tcc atg gac acc gac ctg aac gcg gtc  462
Asp Ile Tyr Leu Val Phe Glu Ser Met Asp Thr Asp Leu Asn Ala Val
     90                  95                 100 atc cag aag ggc aga ctg ttg gag gac atc cac aaa cgt tgc atc ttt  510
Ile Gln Lys Gly Arg Leu Leu Glu Asp Ile His Lys Arg Cys Ile Phe
105                 110                 115 tac cag ctc ctg aga gcc acc aag ttt atc cat tca ggg cgc gtc att  558
Tyr Gln Leu Leu Arg Ala Thr Lys Phe Ile His Ser Gly Arg Val Ile
120                 125                 130                 135 cac cgg gac cag aag cca gcc aac gtt cta ttg gat gct gct tgc cgg  606
His Arg Asp Gln Lys Pro Ala Asn Val Leu Leu Asp Ala Ala Cys Arg
             140                 145                 150 gtg aaa cta tgt gac ttt ggc ctg gca cgc tcc ctc agt gac ttc cct  654
Val Lys Leu Cys Asp Phe Gly Leu Ala Arg Ser Leu Ser Asp Phe Pro
```

```
                    155                 160                 165
gaa ggc ctg ggc cag gcc ctg aca gaa tat gtg gcc aca cgc tgg tac      702
Glu Gly Leu Gly Gln Ala Leu Thr Glu Tyr Val Ala Thr Arg Trp Tyr
            170                 175                 180 cga gct cca gag gtg ctt ctg tct tcc cga tgg tat acc cct ggg gtg      750
Arg Ala Pro Glu Val Leu Leu Ser Ser Arg Trp Tyr Thr Pro Gly Val
    185                 190                 195 gac atg tgg agc ctg ggc tgc ata ctg gga gag atg ctt cga ggg cag      798
Asp Met Trp Ser Leu Gly Cys Ile Leu Gly Glu Met Leu Arg Gly Gln
200                 205                 210                 215 cca ctg ttt ccg ggt aca tct act ttc cac cag ctg gag ctg atc ctg      846
Pro Leu Phe Pro Gly Thr Ser Thr Phe His Gln Leu Glu Leu Ile Leu
                220                 225                 230 gag acc att cca ttg ccc tcc atg gag gag ctc cag ggc ctt gga tca      894
Glu Thr Ile Pro Leu Pro Ser Met Glu Glu Leu Gln Gly Leu Gly Ser
            235                 240                 245 gac tac agt gct ttg att ctg cag aat ctt gga tcc agg cca cgg cag      942
Asp Tyr Ser Ala Leu Ile Leu Gln Asn Leu Gly Ser Arg Pro Arg Gln
        250                 255                 260 acg ctg gac gcc ctc ctg ccg cca gac acc ccc cca gaa gcc ctg gac      990
Thr Leu Asp Ala Leu Leu Pro Pro Asp Thr Pro Pro Glu Ala Leu Asp
265                 270                 275 ctc ctc aag cga ctc ttg gca ttt gct ccg gac aaa cgg ctt agt gca     1038
Leu Leu Lys Arg Leu Leu Ala Phe Ala Pro Asp Lys Arg Leu Ser Ala
280                 285                 290                 295 gag cag gct ctt caa cac cct tac gtg cag aga ttc cat tgc ccc gac     1086
Glu Gln Ala Leu Gln His Pro Tyr Val Gln Arg Phe His Cys Pro Asp
                300                 305                 310 cgc gag tgg aca cgg ggg tcc gat gtg cgg ctc ccg gta cac gaa gga     1134
Arg Glu Trp Thr Arg Gly Ser Asp Val Arg Leu Pro Val His Glu Gly
            315                 320                 325 gac cag ctc tct gca cca gag tat cgc aac cgc ctg tac cag atg atc     1182
Asp Gln Leu Ser Ala Pro Glu Tyr Arg Asn Arg Leu Tyr Gln Met Ile
        330                 335                 340 ctg gag cgg aga cgg aac agc cgc agc cct cga gag gaa gac ttg ggg     1230
Leu Glu Arg Arg Arg Asn Ser Arg Ser Pro Arg Glu Glu Asp Leu Gly
345                 350                 355 gtt gtg gcc tcg cgg gca gag ctc agg gct tcc cag agg caa tcg ctc     1278
Val Val Ala Ser Arg Ala Glu Leu Arg Ala Ser Gln Arg Gln Ser Leu
360                 365                 370                 375 aag ccc gga gtc ctc ccc cag gtc ttg gcg gag acg cct gcg cgg aaa     1326
Lys Pro Gly Val Leu Pro Gln Val Leu Ala Glu Thr Pro Ala Arg Lys
                380                 385                 390 cgc gga ccc aaa cct cag aat ggc cat ggt cac gat ccc gag cat gtg     1374
Arg Gly Pro Lys Pro Gln Asn Gly His Gly His Asp Pro Glu His Val
            395                 400                 405 gaa gtt cgc agg cag agt tca gac ccc ctg tac caa ctt ccg ccg cca     1422
Glu Val Arg Arg Gln Ser Ser Asp Pro Leu Tyr Gln Leu Pro Pro Pro
        410                 415                 420 ggc agc ggg gaa agg ccc cca ggg gcc aca ggg gag cca ccc tcc gca     1470
Gly Ser Gly Glu Arg Pro Pro Gly Ala Thr Gly Glu Pro Pro Ser Ala
                    425                 430                 435 ccc tca ggg gtg aag act cac gtt agg gcg gtg gcg ccc tcc ctg act     1518
Pro Ser Gly Val Lys Thr His Val Arg Ala Val Ala Pro Ser Leu Thr
440                 445                 450                 455 tca cag gcc gcg gct cag gcg gcc aat cag cct ctg atc cgc agt gat     1566
Ser Gln Ala Ala Ala Gln Ala Ala Asn Gln Pro Leu Ile Arg Ser Asp
                460                 465                 470
```

-continued

```
ccg gcc cgg ggc ggt ggg cca agg gct gtc ggc gcg cga cgg gtc cct    1614
Pro Ala Arg Gly Gly Gly Pro Arg Ala Val Gly Ala Arg Arg Val Pro
            475                 480                 485 tcc cgc ctg ccc cgg gag gcc ccg gaa ccc cga ccc ggc cga agg atg    1662
Ser Arg Leu Pro Arg Glu Ala Pro Glu Pro Arg Pro Gly Arg Arg Met
        490                 495                 500 ttt ggc atc tcg gtc tcg cag ggg gcc cag ggt gca gcc aga gct gct    1710
Phe Gly Ile Ser Val Ser Gln Gly Ala Gln Gly Ala Ala Arg Ala Ala
    505                 510                 515 ctt ggc ggc tac tcc cag gcc tac ggg acc gtg tgc cgc tcc gcg ctg    1758
Leu Gly Gly Tyr Ser Gln Ala Tyr Gly Thr Val Cys Arg Ser Ala Leu
520                 525                 530                 535 ggc cgc ctg cct ctg ctc ccc gga ccg cgt gcg tga gccgcccacc         1804
Gly Arg Leu Pro Leu Leu Pro Gly Pro Arg Ala *
                540                 545 aacctccttg cggcaaactg gcgccggccc ccagacccca gcgcatcatc tcccttctct  1864
gcctccccgc cttcgagttc caggagggtt ctctgagcct ctctcccta aggggagta    1924 gatggaggtt tccactccac ccccaacaat ttattccaat aaagttttat ctttcttaaa  1984
aaaaaaaaaa aaaa                                                    1998
```

<210> SEQ ID NO 4
<211> LENGTH: 546
<212> TYPE: PRT
<213> ORGANISM: Rattus norvegicus

<400> SEQUENCE: 4

```
Met Cys Ala Ala Glu Val Asp Arg His Val Ser Gln Arg Tyr Leu Ile
1               5                   10                  15

Lys Arg Arg Leu Gly Lys Gly Ala Tyr Gly Ile Val Trp Lys Ala Met
            20                  25                  30

Asp Arg Arg Thr Gly Glu Val Val Ala Ile Lys Lys Ile Phe Asp Ala
        35                  40                  45

Phe Arg Asp Gln Thr Asp Ala Gln Arg Thr Phe Arg Glu Ile Met Leu
    50                  55                  60

Leu Arg Glu Phe Gly His Pro Asn Ile Ile Arg Leu Leu Asp Val
65                  70                  75                  80

Ile Pro Ala Lys Asn Asp Arg Asp Ile Tyr Leu Val Phe Glu Ser Met
                85                  90                  95

Asp Thr Asp Leu Asn Ala Val Ile Gln Lys Gly Arg Leu Leu Glu Asp
            100                 105                 110

Ile His Lys Arg Cys Ile Phe Tyr Gln Leu Leu Arg Ala Thr Lys Phe
        115                 120                 125

Ile His Ser Gly Arg Val Ile His Arg Asp Gln Lys Pro Ala Asn Val
    130                 135                 140

Leu Leu Asp Ala Ala Cys Arg Val Lys Leu Cys Asp Phe Gly Leu Ala
145                 150                 155                 160

Arg Ser Leu Ser Asp Phe Pro Glu Gly Leu Gly Gln Ala Leu Thr Glu
                165                 170                 175

Tyr Val Ala Thr Arg Trp Tyr Arg Ala Pro Glu Val Leu Leu Ser Ser
            180                 185                 190

Arg Trp Tyr Thr Pro Gly Val Asp Met Trp Ser Leu Gly Cys Ile Leu
        195                 200                 205

Gly Glu Met Leu Arg Gly Gln Pro Leu Phe Pro Gly Thr Ser Thr Phe
    210                 215                 220

His Gln Leu Glu Leu Ile Leu Glu Thr Ile Pro Leu Pro Ser Met Glu
```

```
            225                 230                 235                 240
    Glu Leu Gln Gly Leu Gly Ser Asp Tyr Ser Ala Leu Ile Leu Gln Asn
                    245                 250                 255

Leu Gly Ser Arg Pro Arg Gln Thr Leu Asp Ala Leu Leu Pro Pro Asp
                260                 265                 270

Thr Pro Pro Glu Ala Leu Asp Leu Leu Lys Arg Leu Leu Ala Phe Ala
                275                 280                 285

Pro Asp Lys Arg Leu Ser Ala Glu Gln Ala Leu Gln His Pro Tyr Val
            290                 295                 300

Gln Arg Phe His Cys Pro Asp Arg Glu Trp Thr Arg Gly Ser Asp Val
    305                 310                 315                 320

Arg Leu Pro Val His Glu Gly Asp Gln Leu Ser Ala Pro Glu Tyr Arg
                    325                 330                 335

Asn Arg Leu Tyr Gln Met Ile Leu Glu Arg Arg Asn Ser Arg Ser
                    340                 345                 350

Pro Arg Glu Glu Asp Leu Gly Val Val Ala Ser Arg Ala Glu Leu Arg
                355                 360                 365

Ala Ser Gln Arg Gln Ser Leu Lys Pro Gly Val Leu Pro Gln Val Leu
    370                 375                 380

Ala Glu Thr Pro Ala Arg Lys Arg Gly Pro Lys Pro Gln Asn Gly His
    385                 390                 395                 400

Gly His Asp Pro Glu His Val Glu Val Arg Arg Gln Ser Ser Asp Pro
                    405                 410                 415

Leu Tyr Gln Leu Pro Pro Pro Gly Ser Gly Glu Arg Pro Pro Gly Ala
                420                 425                 430

Thr Gly Glu Pro Pro Ser Ala Pro Ser Gly Val Lys Thr His Val Arg
                435                 440                 445

Ala Val Ala Pro Ser Leu Thr Ser Gln Ala Ala Gln Ala Ala Asn
        450                 455                 460

Gln Pro Leu Ile Arg Ser Asp Pro Ala Arg Gly Gly Pro Arg Ala
    465                 470                 475                 480

Val Gly Ala Arg Arg Val Pro Ser Arg Leu Pro Arg Glu Ala Pro Glu
                    485                 490                 495

Pro Arg Pro Gly Arg Arg Met Phe Gly Ile Ser Val Ser Gln Gly Ala
                500                 505                 510

Gln Gly Ala Ala Arg Ala Ala Leu Gly Gly Tyr Ser Gln Ala Tyr Gly
                515                 520                 525

Thr Val Cys Arg Ser Ala Leu Gly Arg Leu Pro Leu Pro Gly Pro
                530                 535                 540

Arg Ala
    545

<210> SEQ ID NO 5
<211> LENGTH: 15
<212> TYPE: DNA
<213> ORGANISM: Artificial Sequence
<220> FEATURE:
<223> OTHER INFORMATION: oliognucleotide primer

<400> SEQUENCE: 5
accgcagccg cgtct                                                        15

<210> SEQ ID NO 6
<211> LENGTH: 19
<212> TYPE: DNA
<213> ORGANISM: Artificial Sequence
```

```
<220> FEATURE:
<223> OTHER INFORMATION: oliognucleotide primer

<400> SEQUENCE: 6
tctctctcga ggtgccgct                                                   19

<210> SEQ ID NO 7
<211> LENGTH: 26
<212> TYPE: DNA
<213> ORGANISM: Artificial Sequence
<220> FEATURE:
<223> OTHER INFORMATION: oliognucleotide primer

<400> SEQUENCE: 7
tcagatgatc ctggagtgtg gaggca                                           26

<210> SEQ ID NO 8
<211> LENGTH: 21
<212> TYPE: DNA
<213> ORGANISM: Artificial Sequence
<220> FEATURE:
<223> OTHER INFORMATION: oliognucleotide primer

<400> SEQUENCE: 8
cacccccact gaaaaagatg a                                                21

<210> SEQ ID NO 9
<211> LENGTH: 26
<212> TYPE: DNA
<213> ORGANISM: Artificial Sequence
<220> FEATURE:
<223> OTHER INFORMATION: oliognucleotide primer

<400> SEQUENCE: 9
cttaactatc ttgggctgtg acaaag                                           26

<210> SEQ ID NO 10
<211> LENGTH: 24
<212> TYPE: DNA
<213> ORGANISM: Artificial Sequence
<220> FEATURE:
<223> OTHER INFORMATION: oliognucleotide primer

<400> SEQUENCE: 10
tatgcctgcc gtgtgaacca cgtg                                             24

<210> SEQ ID NO 11
<211> LENGTH: 17
<212> TYPE: PRT
<213> ORGANISM: Artificial Sequence
<220> FEATURE:
<223> OTHER INFORMATION: consensus sequence involved in ATP binding
<221> NAME/KEY: VARIANT
<222> LOCATION: (1)...(1)
<223> OTHER INFORMATION: The L can also be I or V
<221> NAME/KEY: VARIANT
<222> LOCATION: (3)...(3)
<223> OTHER INFORMATION: Xaa = Any Amino Acid other than P
<221> NAME/KEY: VARIANT
<222> LOCATION: (5)...(5)
<223> OTHER INFORMATION: Xaa = Any amino acid other than P
<221> NAME/KEY: VARIANT
<222> LOCATION: (6)...(6)
<223> OTHER INFORMATION: The F can also be Y, W, M, G, S, T, N, or H
<221> NAME/KEY: VARIANT
<222> LOCATION: (7)...(7)
<223> OTHER INFORMATION: The S can also be G or A
<221> NAME/KEY: VARIANT
<222> LOCATION: (8)...(8)
```

```
<223> OTHER INFORMATION: Xaa = Any amino acid other than P and W
<221> NAME/KEY: VARIANT
<222> LOCATION: (9)...(9)
<223> OTHER INFORMATION: The L can also be I, V, C, A, or T
<221> NAME/KEY: VARIANT
<222> LOCATION: (10)...(10)
<223> OTHER INFORMATION: Xaa = Any amino acid other than P and D
<221> NAME/KEY: VARIANT
<222> LOCATION: (11)...(11)
<223> OTHER INFORMATION: Xaa = Any amino acid
<221> NAME/KEY: VARIANT
<222> LOCATION: (12)...(12)
<223> OTHER INFORMATION: The G can also be S, T, A, C, L, I, V, M, F, or
      Y
<221> NAME/KEY: VARIANT
<222> LOCATION: (13)...(13)
<223> OTHER INFORMATION: Xaa = The next 5-18 amino acids can be any amino
      acid
<221> NAME/KEY: VARIANT
<222> LOCATION: (14)...(14)
<223> OTHER INFORMATION: The L can also be I, V, M, F, Y, W, C, S, T, A,
      or R
<221> NAME/KEY: VARIANT
<222> LOCATION: (15)...(15)
<223> OTHER INFORMATION: The A can also be I, V, or P
<221> NAME/KEY: VARIANT
<222> LOCATION: (16)...(16)
<223> OTHER INFORMATION: The L can also be I, V, M, F, A, G, C, K, or R

<400> SEQUENCE: 11

Leu Gly Xaa Gly Xaa Phe Ser Xaa Leu Xaa Xaa Gly Xaa Leu Ala Leu
  1               5                  10                  15

Lys

<210> SEQ ID NO 12
<211> LENGTH: 13
<212> TYPE: PRT
<213> ORGANISM: Artificial Sequence
<220> FEATURE:
<223> OTHER INFORMATION: consensus sequence for the serine/threonine
      kinases
<221> NAME/KEY: VARIANT
<222> LOCATION: (1)...(1)
<223> OTHER INFORMATION: The L at position 1 can be I, V, M, F, Y, or C.
<221> NAME/KEY: VARIANT
<222> LOCATION: (2)...(2)
<223> OTHER INFORMATION: The X at position 2 can be any amino acid.
<221> NAME/KEY: VARIANT
<222> LOCATION: (3)...(3)
<223> OTHER INFORMATION: The H at position 3 can be Y.
<221> NAME/KEY: VARIANT
<222> LOCATION: (6)...(6)
<223> OTHER INFORMATION: The L at position 6 can be I, V, M, F or Y.
<221> NAME/KEY: VARIANT
<222> LOCATION: (8)...(8)
<223> OTHER INFORMATION: The X at position 8 can be any amino acid.
<221> NAME/KEY: VARIANT
<222> LOCATION: (9)...(9)
<223> OTHER INFORMATION: The X at position 9 can be any amino acid.
<221> NAME/KEY: VARIANT
<222> LOCATION: (11)...(11)
<223> OTHER INFORMATION: The L at position 11 can be I, V, M, F, Y, C,
      or T.
<221> NAME/KEY: VARIANT
<222> LOCATION: (12)...(12)
<223> OTHER INFORMATION: The L at position 12 can be I, V, M, F, Y, C,
      or T.
<221> NAME/KEY: VARIANT
<222> LOCATION: (13)...(13)
<223> OTHER INFORMATION: The L at position 13 can be I, V, M, F, Y, C,
      or T.
<221> NAME/KEY: VARIANT
<222> LOCATION: (4)...(4)
<223> OTHER INFORMATION: The X at position 4 can be any amino acid.

<400> SEQUENCE: 12
```

```
Leu Xaa His Xaa Asp Leu Lys Xaa Xaa Asn Leu Leu Leu
 1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: consensus sequence for tyrosine kinases
<221> NAME/KEY: VARIANT
<222> LOCATION: (1)...(1)
<223> OTHER INFORMATION: The L at position 1 can also be I, V, M, F, Y,
      or C.
<221> NAME/KEY: VARIANT
<222> LOCATION: (2)...(2)
<223> OTHER INFORMATION: The X at position 2 can be any amino acid.
<221> NAME/KEY: VARIANT
<222> LOCATION: (3)...(3)
<223> OTHER INFORMATION: The H at position 3 can be Y.
<221> NAME/KEY: VARIANT
<222> LOCATION: (6)...(6)
<223> OTHER INFORMATION: The L at position 6 can be I, V, M, F, or Y.
<221> NAME/KEY: VARIANT
<222> LOCATION: (7)...(7)
<223> OTHER INFORMATION: The R at position 7 can be S, T, A or C.
<221> NAME/KEY: VARIANT
<222> LOCATION: (8)...(8)
<223> OTHER INFORMATION: The X at position 8 can be any amino acid
<221> NAME/KEY: VARIANT
<222> LOCATION: (9)...(9)
<223> OTHER INFORMATION: The X at position 9 can be any amino acid
<221> NAME/KEY: VARIANT
<222> LOCATION: (11)...(11)
<223> OTHER INFORMATION: The L at position 11 can be I, V, M, F, Y or C.
<221> NAME/KEY: VARIANT
<222> LOCATION: (12)...(12)
<223> OTHER INFORMATION: The L at position 12 can be I, V, M, F, Y or C.
<221> NAME/KEY: VARIANT
<222> LOCATION: (13)...(13)
<223> OTHER INFORMATION: The L at position 13 can be I, V, M, F, Y or C.
<221> NAME/KEY: VARIANT
<222> LOCATION: (4)...(4)
<223> OTHER INFORMATION: The X at position 4 can be any amino acid.

<400> SEQUENCE: 13

```
Leu Xaa His Xaa Asp Leu Arg Xaa Xaa Asn Leu Leu Leu
 1               5                   10
```